US010595748B2

(12) United States Patent
Kubiak et al.

(10) Patent No.: US 10,595,748 B2
(45) Date of Patent: *Mar. 24, 2020

(54) SYSTEMS, DEVICES, AND METHODS FOR PROVIDING FOOT LOADING FEEDBACK TO PATIENTS AND PHYSICIANS DURING A PERIOD OF PARTIAL WEIGHT BEARING

(71) Applicants: Erik N. Kubiak, Salt Lake City, UT (US); Kylee North, Bountiful, UT (US); Tomasz Petelenz, Salt Lake City, UT (US); Robert W. Hitchcock, Sandy, UT (US)

(72) Inventors: Erik N. Kubiak, Salt Lake City, UT (US); Kylee North, Bountiful, UT (US); Tomasz Petelenz, Salt Lake City, UT (US); Robert W. Hitchcock, Sandy, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 1181 days.

This patent is subject to a terminal disclaimer.

(21) Appl. No.: 13/757,559

(22) Filed: Feb. 1, 2013

(65) Prior Publication Data

US 2013/0150755 A1 Jun. 13, 2013

Related U.S. Application Data

(63) Continuation-in-part of application No. 13/178,314, filed on Jul. 7, 2011, now Pat. No. 8,758,273, which
(Continued)

(51) Int. Cl.
*A61B 5/103* (2006.01)
*A61B 5/00* (2006.01)
*A61B 5/11* (2006.01)

(52) U.S. Cl.
CPC .......... *A61B 5/1036* (2013.01); *A61B 5/1038* (2013.01); *A61B 5/11* (2013.01);
(Continued)

(58) Field of Classification Search
CPC ... A61B 5/1036; A61B 5/1038; A61B 5/4833; A61B 5/486; A61B 5/6807;
(Continued)

(56) References Cited

U.S. PATENT DOCUMENTS

| 5,042,504 A | 8/1991 | Huberti |
| 5,269,081 A | 12/1993 | Gray |

(Continued)

FOREIGN PATENT DOCUMENTS

| DE | 19804443 | 8/1999 |
| EP | 1702560 | 9/2006 |

(Continued)

OTHER PUBLICATIONS

U.S. Appl. No. 13/178,314, Mar. 21, 2014, Notice of Allowance.
(Continued)

*Primary Examiner* — Devin B Henson
(74) *Attorney, Agent, or Firm* — Workman Nydegger

(57) ABSTRACT

Systems, devices, and methods for providing user feedback regarding compliance with a set of partial weight bearing (PWB) criteria are described. A computer system receives force data from a non-compressible force transmitter that is assigned to a user, and accesses the force data received from the non-compressible force transmitter to determine whether the user is within a predefined pressure compliance range. The pressure compliance range specifies a prescribed range of pressure that is to be applied during a PWB period. The computer system then receives a compliance data request from the user or the user's physician and communicates compliance data representing the user's compliance with the
(Continued)

prescribed range of pressure during the PWB period to the user and/or the user's physician.

19 Claims, 17 Drawing Sheets

Related U.S. Application Data is a continuation-in-part of application No. 12/833,214, filed on Jul. 9, 2010, now Pat. No. 8,758,272.

(60) Provisional application No. 61/632,879, filed on Feb. 1, 2012, provisional application No. 61/617,204, filed on Mar. 29, 2012.

(52) U.S. Cl.
CPC ............ *A61B 5/486* (2013.01); *A61B 5/4833* (2013.01); *A61B 5/6807* (2013.01); *A61B 5/6829* (2013.01); *A61B 5/7275* (2013.01); *A61B 5/742* (2013.01); *A61B 5/746* (2013.01); *A61B 5/7475* (2013.01); *A61B 5/0002* (2013.01); *A61B 5/743* (2013.01); *A61B 2562/0247* (2013.01); *A61B 2562/0252* (2013.01)

(58) Field of Classification Search
CPC ....... A61B 5/6829; A61B 5/746; A61B 5/743; A61B 2562/0247; A61B 2562/0252
See application file for complete search history.

(56) References Cited

U.S. PATENT DOCUMENTS

| | | | |
|---|---|---|---|
| 5,357,696 A | 10/1994 | Gray | |
| 5,359,791 A | 11/1994 | Prahl | |
| 5,452,527 A | 9/1995 | Gaylord | |
| 5,813,142 A * | 9/1998 | Demon | A43B 3/0005 36/28 |
| 6,931,938 B2 | 8/2005 | Knirck | |
| 7,426,873 B1 * | 9/2008 | Kholwadwala | A43B 3/00 73/777 |
| 7,610,802 B2 | 11/2009 | Clar | |
| 8,280,681 B2 | 10/2012 | Vock | |
| 9,005,140 B2 * | 4/2015 | Mann | A61B 5/1038 600/587 |
| 2002/0095105 A1 | 7/2002 | Jensen | |
| 2003/0163287 A1 | 8/2003 | Vock et al. | |
| 2004/0034289 A1 * | 2/2004 | Teller | A61B 5/02055 600/300 |
| 2005/0172517 A1 | 8/2005 | Bledsoe | |
| 2005/0217142 A1 | 10/2005 | Frampton | |
| 2010/0280629 A1 | 11/2010 | Jung | |
| 2010/0324455 A1 | 12/2010 | Rangel et al. | |
| 2011/0054359 A1 | 3/2011 | Sazonov | |
| 2011/0214501 A1 * | 9/2011 | Ross | A43B 3/0005 73/172 |
| 2011/0319755 A1 * | 12/2011 | Stein | A61B 5/0031 600/437 |
| 2012/0010534 A1 | 1/2012 | Kubiak et al. | |
| 2012/0010535 A1 | 1/2012 | Kubiak et al. | |
| 2012/0015035 A1 | 1/2012 | Nubiak | |
| 2012/0255160 A1 * | 10/2012 | Boone | A61B 5/1038 29/592 |

FOREIGN PATENT DOCUMENTS

| | | | |
|---|---|---|---|
| EP | 1494626 | 11/2006 | |
| EP | 1519701 | 12/2009 | |
| LU | 91810 | * 4/2011 | .......... A43B 3/0005 |
| WO | 2013006445 | 1/2013 | |

OTHER PUBLICATIONS

European Search Report for EP12807044 dated Dec. 15, 2014, 7 pages.
European Search Report for EP14153642 dated Apr. 11, 2014, 3 pages.
Hessert, Mary J. et al., "Foot Pressure Distribution During Walking in Young and Old Adults," *BMC Geriatrics*, vol. 5, p. 8, May 19, 2005.
Authier, A. et al., "A Proof of Concept for a Wireless Ambulatory Weight Bearing Measurement System in Rehabilitation and Telerehabilitation Applications," Third IEEE International Conference on *Wireless and Mobile Computing, Networking and Communications*, Oct. 2007, pp. 73-80.
Lawrence, T.L. et al., "Wireless In-Shoe Force System [For Motor Prosthesis]," *Engineering in Medicine and Biology Society*, Oct./Nov. 1997, vol. 5, pp. 2238-2241.
Kaplan, Yonatan, "The Use of a New Biofeedback Insole Weight-Bearing Measuring Device in the Assessment and Rehabilitation of Soccer Players: A Case Study Review," *Journal of Sports Science and Medicine* 2007, Suppl. 10, 5 pages.
"The Quality In-Shoe Dynamic Pressure Measuring System," Accessed at http://www.novel.de/novelcontent/pedar on Jul. 30, 2013, 16 pages.
Honeywell, Model 1865 Series Force/ Pressure Tranducer, Apr. 2005, pp. 1-4.
North, Kylee "A Novel Load Sensor for Improving Tibial Fracture Outcomes," University of Utah Masters of Science Thesis, May 2010, 40 pages.
Kubiak, et al., PCT/US2012/044966 International Search Report Dated Sep. 12, 2012, 3 pages.
Kubiak, et al., PCT/US2012/044966 Written Opinion Dated Sep. 12, 2012, 5 pages.
U.S. Appl. No. 12/833,214, Sep. 29, 2011, Office Action.
U.S. Appl. No. 13/178,314, Nov. 27, 2012, Office Action.
U.S. Appl. No. 12/833,214, dated Feb. 19, 2014, Notice of Allowance.
North et al., "An Insole Sensor for Recording Weight Bearing Behavior During Tibial Fracture Rehabilitation," 2010 Annual International Conference of the IEEE Engineering in Medicine and Biology Society, 2010, pp. 1856-1859.

\* cited by examiner

SYSTEMS, DEVICES, AND METHODS FOR PROVIDING FOOT LOADING FEEDBACK TO PATIENTS AND PHYSICIANS DURING A PERIOD OF PARTIAL WEIGHT BEARING

CROSS-REFERENCE TO RELATED APPLICATIONS

This application is a continuation-in-part of, and claims the benefit of and priority to, U.S. patent application Ser. No. 13/178,314, filed on Jul. 7, 2011, and entitled "SYSTEMS, DEVICES, AND METHODS FOR MONITORING AN UNDER FOOT LOAD PROFILE OF A PATIENT DURING A PERIOD OF PARTIAL WEIGHT BEARING", which itself is a continuation-in-part of, and claims the benefit of and priority to, U.S. patent application Ser. No. 12/833,214, filed on Jul. 9, 2010, and entitled "SYSTEMS, DEVICES, AND METHODS FOR MONITORING AN UNDER FOOT LOAD PROFILE OF A TIBIAL FRACTURE PATIENT DURING A PERIOD OF PARTIAL WEIGHT BEARING", which applications are both hereby expressly incorporated herein by reference in their entirety.

This application also claims priority to and the benefit of U.S. Provisional Patent Application Ser. No. 61/632,879, filed on Feb. 1, 2012, entitled "EFFECTS OF KNEE-HIGH WALKING BOOT CASTS ON PEAK PLANTAR LOADS", and U.S. Provisional Patent Application Ser. No. 61/617,204, filed on Mar. 29, 2012, entitled "SYSTEMS, DEVICES, AND METHODS FOR PROVIDING FOOT LOADING FEEDBACK TO PATIENTS AND PHYSICIANS DURING A PERIOD OF PARTIAL WEIGHT BEARING", which applications are both hereby expressly incorporated herein by reference in their entirety.

BACKGROUND

1. The Field of the Disclosure

The present disclosure relates generally to systems, devices, and methods for measuring under foot load profiles. More particularly, the disclosure relates to systems, devices, and methods for monitoring an under foot load profile of a patient during a period of partial weight bearing (PWB).

2. The Relevant Technology

Bone fractures, or broken bones, may be caused by direct or indirect forces to a bone, or as a result of certain medical conditions, such as osteoporosis. Falls, sports injuries, and motor vehicle accidents are common causes of fractures. Fractures can be very painful, can take significant time to heal, and can result in significant costs.

For instance, the tibia, which is the most commonly broken long bone in the body, typically requires between about ten weeks and about ten months to heal completely. By some estimates, the number and severity of complications associated with tibial fractures results in an annual direct cost for the United States of about $1.2 billion USD. When indirect costs such as lost wages are factored, in the long rehabilitation period for tibial fracture patients results in an estimated annual indirect cost of about $95 billion USD.

The mechanical environment experienced by the recovering bone is a major factor in fracture healing rate. In an attempt to produce an optimal mechanical environment that promotes bone healing while reducing risk of complications, clinicians routinely prescribe PWB during fracture rehabilitation. For example, PWB is commonly prescribed during rehabilitation of hip and lower extremity injuries, such as fractures to hips, femurs, tibias, ankles, calcanei, metatarsals, and the like.

The PWB prescription for a patient varies based on the type and extent of the injury and on the discretion of the clinician. Unfortunately, little data has been collected to support a conclusion that PWB prescriptions are effective at either promoting fracture healing or reducing the risk of complications. Additionally, the patients' tendencies or abilities to comply with the PWB prescription for the entire duration between follow-up visits are unknown. Therefore, clinicians and researchers would greatly benefit from a load monitoring device that can continually track the PWB behavior of a patient between follow-up visits. As follow-up visits may be scheduled one day, a week, or even two-weeks apart, clinicians and researches would greatly benefit from a robust monitoring device capable of tracking the PWB behavior even over extended periods of time.

The subject matter claimed herein is not limited to embodiments that solve any disadvantages or that operate only in environments such as those described. Rather, this background is only provided to illustrate one exemplary technology area where some embodiments described herein may be practiced.

BRIEF SUMMARY

The present disclosure relates generally to systems, devices, and methods for measuring under foot load profiles. More particularly, the disclosure relates to systems, devices, and methods for monitoring an under foot load profile of a fracture patient during a period of partial weight bearing (PWB).

An embodiment of the present disclosure relates to a system for measuring an under foot load profile of a fracture patient during a period of PWB, and includes a housing, pressure sensor, and non-compressible force transmitter. The housing may be oriented with respect to a patient's fractured bone and defines a cavity. The pressure sensor is configured to monitor the load profile of the fracture patient during the desired period of PWB, and the pressure sensor is located at least partially within the cavity. A non-compressible force transmitter within the cavity is adjacent the pressure sensor so as to transmit pressure within the housing.

In some embodiments, the pressure sensor is fully encapsulated within the non-compressible force transmitter. Moreover, the pressure sensor may include a piezoresistive Wheatstone bridge pressure sensor or other similarly capable sensor. The non-compressible force transmitter may be silicone gel or another silicone-based composition.

According to some embodiments of the present disclosure, a movable piston is connected to a non-compressible force transmitter. A piston may, for instance, include a surface that is movable relative to the housing, and such movement can correspond to a pressure applied to, or transmitted from, a pressure sensor. In at least some embodiments, a lower-leg immobilizer such as a walking boot cast is included with the system. When the system includes a lower-leg immobilizer, the housing may be at least partially located in a heel or ball region of the lower-leg immobilizer. The housing may also be placed at other locations along the plantar surface. In some other embodiments, the housing may be incorporated into any lower leg orthosis other than a walking boot cast, such as any ankle foot orthosis, a hard or other cast, a camwalker, hard sole shoes, cast shoes, or a patient's regular footwear. For instance, the housing may be configured as an insole insert that may be selectively placed in various types of footwear.

In some cases, the pressure sensor is located within a lower portion of the cavity of the housing, and optionally at least proximate a lower internal surface of the housing. The pressure sensor can be positioned relative to the non-compressible force transmitter so as to receive a pressure applied to the housing from the non-compressible force transmitter. The pressure sensor may also transmit a received pressure to an inner contact surface of the housing, although the pressure sensor may additionally or alternatively transmit a received pressure to the non-compressible force transmitter.

In operation, a housing may define an aperture in at least a portion thereof. For instance, the aperture may provide a reference pressure for determining a load profile. A reference pressure may include an absolute pressure, and a load profile can be determined as a relative pressure differential. A storage device is optionally included in the device. A storage device may be configured to receive a measure of a load profile from the pressure sensor. The storage device may be integral with, local to, or remote from the pressure sensor. In some cases, an aperture in the housing is used for a communication device that couples the pressure sensor to the storage device. In still other embodiments, the pressure sensor is configured for wireless communication with the storage device.

During a period of PWB, the pressure sensor potentially provides continuous monitoring and/or transmission of the load profile to the storage device. Such monitoring may be over the full period of PWB, and can be periodic or continuous. For instance, the pressure sensor may continuously obtain substantially uninterrupted results over the full period of PWB. The pressure sensor may alternatively obtain periodic results over the full period of PWB.

In accordance with another example embodiment, a method is performed for measuring an under foot load profile of a bone fracture patient during a period of PWB. In at least some aspects, a method may include substantially immobilizing a bone of a bone fracture patient. A housing may be oriented relative to the patient's bone, and the housing optionally defines a cavity. A non-compressible force transmitter may be positioned within the cavity and as a load is applied to the housing, the load can be transmitted as a pressure to the non-compressible force transmitter. The load profile generated by applying the load to the housing may be monitored using a pressure sensor at least proximate the non-compressible force transmitter. In some cases the pressure sensor is within or adjacent the non-compressible force transmitter.

As the load profile is generated, the load profile can be stored. For instance, the load profile can be stored locally within the housing or external thereto. The load profile may generally correspond to the pressure applied by the non-compressible force transmitter to the pressure sensor, such as when the pressure sensor is adjacent the force transmitter. In accordance with some aspects, the pressure sensor is substantially fully encapsulated within the force transmitter.

As the load profile is monitored, the load profile can be measured, stored, or otherwise monitored, or have any combination of the foregoing performed. Monitoring the load profile can include monitoring the load profile over a first period of time. That first period of time may be about an hour, about a day, about a week, about two weeks, and/or about four to six weeks. For instance, the first period of time may correspond to a time between scheduled visits with a physician or clinician. During such time, monitoring of the load profile may be continuous and substantially uninterrupted. Monitoring the load over the first period of time may also include periodically monitoring the load for a second period of time within the first period of time. Prior to monitoring the load, the applied load may first be detected.

In accordance with another embodiment, a method for treating a bone fracture patient during a period of PWB includes substantially immobilizing the bone of the patient. A load can be applied to a housing that defines a cavity having a flexible, non-compressible force transmitter at least partially disposed within the cavity. The load can then be monitored, and the load profile can be generated by applying the load to the housing. Monitoring may be facilitated by using a pressure sensor linked to the force transmitter, such that the load generates a pressure within the non-compressible force transmitter, and that force is then transmitted to the pressure sensor.

When a pressure sensor is used to monitor the load profile, the pressure sensor may be located at least partially within the force transmitter or at least proximate thereto. In some embodiments, the pressure sensor is substantially fully enclosed within the force transmitter. In other embodiments, the pressure sensor may be at least partially external to the force transmitter.

As the load profile is monitored, the period of PWB can be adjusted. Such adjustments may be based on the monitored load profile. For instance, the period may be increased or reduced based on the load profile. A pressure sensor used to monitor the load profile may be calibrated. In some cases, the calibration may be performed a single time such that monitoring the load profile is performed without recalibration after first applying the load to the housing.

In accordance with another example embodiment, a system for measuring a load profile of bone fracture patient is produced. Production of such system may include forming a housing that defines a cavity. A non-compressible force transmitter may be positioned at least partially within the cavity, and a pressure sensor can be positioned at least partially within the housing. The housing can be positioned within the footprint of a bone immobilizer configured to substantially immobilize a bone.

The pressure sensor can be positioned to be in the line-of-action of an applied load or pressure. In some cases, the pressure can be applied from any direction, and the pressure sensor can be at least partially enclosed within the force transmitter. For instance, the force transmitter may include a silicone gel that is optionally cured. An applied load may be transmitted through the silicone gel as a pressure that can be monitored from any direction or orientation within the gel. A pressure sensor can be fully enclosed within the gel to measure the pressure. In certain embodiments, the bone is immobilized by a lower-leg immobilizer. The housing may be positioned within a heel region or at least partially between a fourth and fifth metatarsal head portion of the lower-leg immobilizer.

In one embodiment, a computer-implemented method is provided for providing user feedback regarding compliance with a set of partial weight bearing (PWB) criteria. A computer system receives force data from a non-compressible force transmitter that is assigned to a user and accesses the force data received from the non-compressible force transmitter to determine whether the user is within a predefined pressure compliance range. The pressure compliance range specifies a prescribed range of pressure that is to be applied during a PWB period. The computer system then receives a compliance data request from the user or the user's physician and wirelessly communicates compliance data representing the user's compliance with the prescribed range of pressure during the PWB period to the user and/or the user's physician.

In another embodiment, a computer system is provided that gathers and stores force data to determine users' compliance with a predefined pressure compliance range. The computer system receives an indication that a period of partial weight bearing (PWB) has been initiated for a user and initiates a non-compressible force transmitter that is assigned to the user. The non-compressible force transmitter is positioned both within a cavity of a housing oriented with respect to the user's leg and adjacent to a pressure sensor to transmit pressure within the housing. The computer system stores, at specified intervals, force data sensed by the pressure sensor, which indicates the user's compliance with a prescribed range of pressure that is to be applied during the PWB period. Then, upon receiving a request for stored force data, the computer system sends the stored force data to the data requester.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Moreover, it is contemplated that each feature identified in this Summary may be independently included with any other one or more features identified herein, unless such feature is expressly described as requiring use with one or more particular other features, or by its nature cannot be used in combination with other features herein.

Additional features and advantages will be set forth in the description which follows, and in part will be obvious from the description, or may be learned by the practice of the teachings herein. Features and advantages of the present disclosure may be realized and obtained by means of the instruments and combinations particularly pointed out in the appended claims. Features of the present disclosure will become more fully apparent from the following description and appended claims, or may be learned by the practice of the disclosed embodiments as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

While certain devices may be available and allow analysis of insole pressure, gait pathology, or plantar ulcer prevention in diabetic patients, such devices fail to provide continuous monitoring and/or recording of the load placed on an injured limb. Moreover, such devices are generally confined to monitoring over a short time span, and fail to allow for continuous monitoring and/or recording of a load over longer periods of time, such as greater than one hour. Often, such devices may be limited in part by the performance of their sensor technology. For example, capacitive resistors, polymer sheet or ink based force-sensing resistors, pneumatically coupled systems connected to a pressure sensor, or general force-sensing resistors may suffer from limitations such as hysteresis, creep non-linearity, poor dynamic response, temperature effects, non-linearity, poor durability, or other limitations, or any combination of the foregoing. Although insole pressure and/or gait analysis devices may be useful for their intended purposes, these systems may be limited in their ability to record the load placed on a limb for an extended period. Furthermore, such systems are generally very expensive.

To provide an economic solution to measuring the mechanical environment produced by partial weight bearing (PWB), the present application relates generally to a durable, low cost load sensor that can record the load placed on an injured limb over an extended period such as over a two-week or four-week period. The use of such load sensors—including micromachined silicon piezoresistive pressure sensors—may provide an accurate and durable load sensor that is economic, robust, and capable of accurately measuring the normal loads experienced by an immobilized limb. Thus, embodiments disclosed herein or which may be learned from a practice of the disclosure set forth herein may include systems, devices, and methods for monitoring an under foot load profile of a patient during a period of PWB. At least one embodiment of a system described herein may enable clinicians to understand how PWB may be used to direct patient outcomes, thereby potentially reducing healing time and complications for various maladies, such as bone fractures or other maladies.

A load profile may generally include an estimation of the amount of weight borne by all or a portion of a patient's lower-leg. For example, during a period of PWB, the load profile may reflect aspects of the loading on the lower leg. The load profile may reflect data or information such as maximum and minimum loads placed on the lower leg, average load placed on the lower leg, load duration, the total load over time, other aspects, or combinations thereof.

Figure 1:
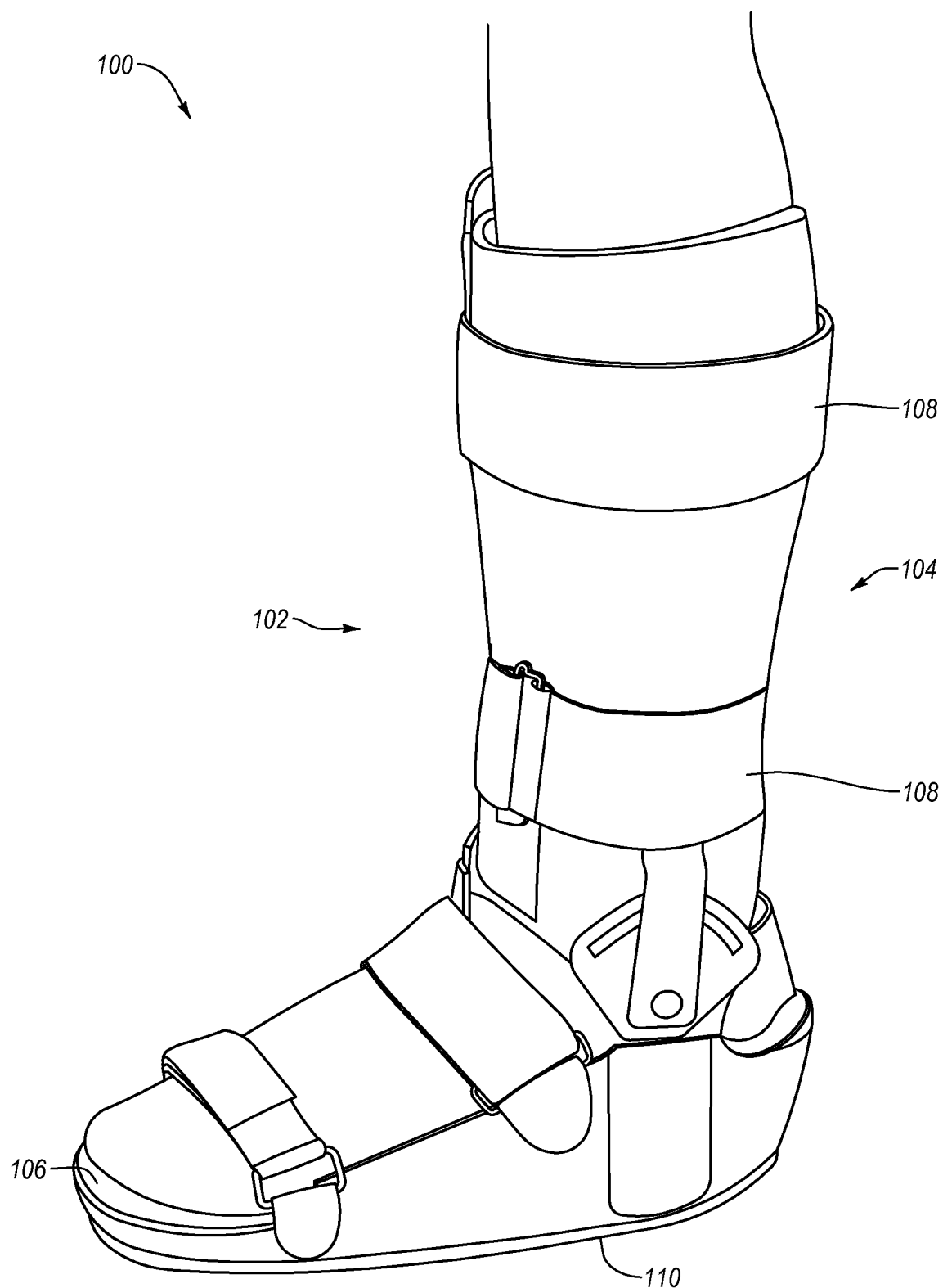
FIG. 1 illustrates a schematic representation of a system for measuring an under foot profile of a patient during a period of partial weight bearing (PWB) according to an exemplary embodiment of the present disclosure.

Turning now to FIG. 1, a schematic representation is provided for a system 100 for measuring an under foot profile of a tibial fracture patient during a period of PWB, in accordance with at least one exemplary embodiment of the present disclosure. While the following description refers to a tibial fracture patient, the present invention is not limited for use with only tibial fracture patients. Rather, the present invention may be configured for measuring an under foot profile of any person, regardless of whether that person has suffered a tibial fracture, other bone fracture, non-fracture injury, or no injury at all. Thus, while much of the following discussion refers to tibial fractures, it will be appreciated that such references are made merely by way of example and not limitation.

Generally after post-fracture edema or swelling has subsided, a tibial fracture patient may be prescribed a period of PWB. In order to stimulate osteogenesis while minimizing mechanical forces on the break, a PWB prescription may include the use of a lower-leg immobilizer 102. In some embodiment, the lower-leg immobilizer 102 may take the form of a walking boot cast, although other types of devices may also be used. For example, any lower leg orthosis, such as any ankle foot orthosis, a hard or other cast boot, a camwalker, hard sole shoes, cast shoes, or a patient's regular footwear may be used. Additionally, in some cases, a PWB prescription may exclude the use of a lower-leg immobilizer 102 and/or may include the use of another orthotic device.

As shown in FIG. 1, a lower-leg immobilizer 102 may include a force distribution section 104 and/or a foot bed 106. When the lower-leg immobilizer 102 is placed on the patient's leg, the patient's foot may be oriented with respect to, and optionally supported upon, the foot bed 106. Accordingly, in some embodiments the foot bed 106 may be sized, shaped, contoured, or otherwise configured to allow a patient to comfortably support his or her foot thereon. Further, the foot bed 106 may be oversized or otherwise configured in some embodiments so as to accommodate feet of different sizes, although the foot bed 106 may also be customized for a particular patient or foot size.

The force distribution section 104 may be used to distribute forces generated by or within the lower-leg immobilizer. For instance, as a patient places his or her weight on the leg, the patient's weight can generate a load that may be transferred to the foot bed 106. Ultimately, the load may be transferred through the force distribution section 104. Within the force distribution section 104, one or more retention straps 108 are optionally included. Such retention straps may facilitate distribution of the load and/or retention or support of the patient's lower leg. Distributing the forces generated during a period of PWB may facilitate accelerated healing of the patient's fracture.

The lower-leg immobilizer 102 may include various features in addition to those described herein. For example, the lower-leg immobilizer 102 may include shock absorption features, positioning features, traction devices, other features, or combinations thereof. One example additional feature may include modification of the tread 110. Rocker treads, softer materials, or other features may improve the tread 110 for traction and/or shock absorption aspects related to the lower-leg immobilizer 102.

Figure 2:
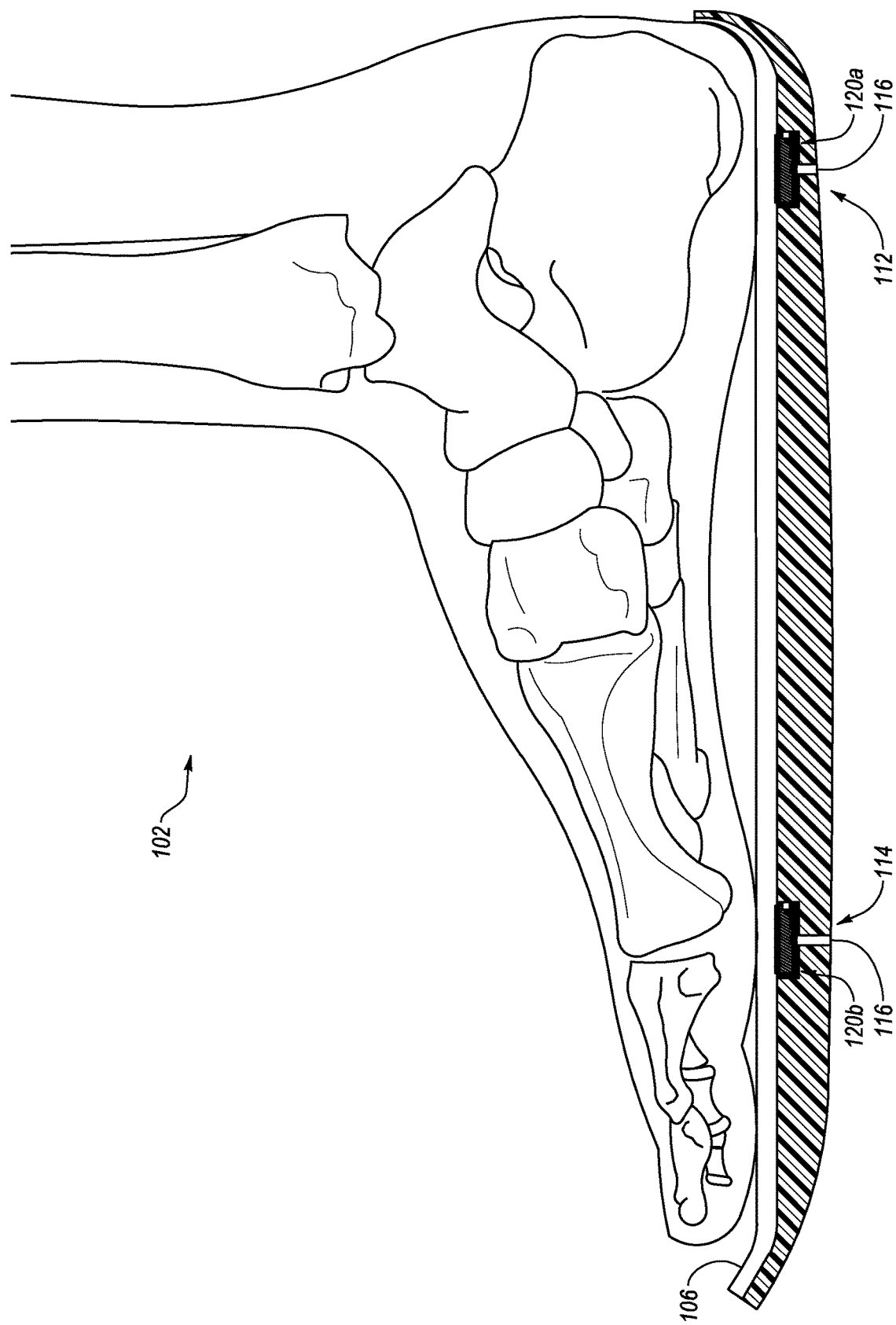
FIG. 2 illustrates a cutaway perspective view of the embodiment of the system of FIG. 1.

FIG. 2 illustrates a cutaway, slight perspective view of an example system for measuring an under foot profile of a tibial fracture patient during a period of PWB, and may in some aspects be used in connection with the system 100 of FIG. 1. Specifically, FIG. 2 generally illustrates a foot bed 106 of a lower-leg immobilizer 102. Although the foot bed 106 is identified as a part of the lower-leg immobilizer 102, in instances where the PWB prescription excludes the use of a lower-leg immobilizer 102, the foot bed 106 may be a part of another orthotic device. For example, another orthotic device may include a foot bed or support similar to foot bed 106, but may exclude the force distribution section 104 (see FIG. 1) or other similar feature or section.

In order to use the lower-leg immobilizer 102 to measure, analyze, store, or otherwise monitor a load profile of a PWB patient, at least one load profile monitoring device 120a, 120b may be located relative to the foot bed 106 and/or the patient. Generally, as a user walks, peak forces are experienced at the heel of the foot during mid-stance and at about the fourth and fifth metatarsal heads during toe-off. Thus, in accordance with some embodiments, and as illustrated in FIG. 2, a first load profile monitoring device 120a may be located in the heel region 112 of the foot bed 106 and/or a second load profile monitoring device 120b may be located in the ball region 114 of the foot bed 106, which ball region may be situated about in the region of the fourth and fifth metatarsal heads. In other embodiments, a single load profile monitoring device may be sized and/or configured to measure the load profile in both the ball region 114 and the heel region 112, or may be otherwise located relative to a patient's foot or the foot bed 106. In further embodiments, more and/or fewer load profile monitoring devices may be used in various locations of the foot bed 106. For instance, a single load monitoring device may be used at either the heel region 112 or in the ball region 114 of the foot bed 106. In still other embodiments, one or more load monitoring devices are located at other locations relative to the foot bed.

In the illustrated embodiment, an aperture 116 is provided for each load profile monitoring device 120a, 120b. In accordance with some embodiments, the apertures 116 may be used as reference apertures to facilitate obtaining of a reference pressure measurement (e.g., atmospheric pressure). For instance, as discussed herein, a load profile monitoring device 120a, 120b may include a pressure sensor that utilizes an absolute or other reference pressure to determine a relative pressure differential as part of a load profile. The apertures 116 may thus be open and exposed to the environment so as to have access to atmospheric pressure. While the apertures 116 are shown as being open, one skilled in the art will appreciate that such apertures 116 are, however, merely exemplary. In other embodiments, for instance, one or more protective features may be used to limit contaminants or other materials through the apertures 116. By way of illustration, a mesh, air-permeable foam, or other material, or any combination of the foregoing, may be included on or within the apertures 116 to provide protection against contaminants.

While FIG. 2 illustrates the use of apertures 116 extending in a generally vertical direction through the foot bed 106, it should be appreciated that such feature is merely exemplary. For instance, in other embodiments the apertures 116 may be eliminated, moved, or otherwise configured. In one exemplary embodiment, for example, the apertures 116 can be eliminated and a pressure or other aspect can be measured or otherwise monitored using a reference pressure other than atmospheric pressure. In still other embodiments, an absolute pressure may be used as a gauge to measure or monitor a load profile. For instance, each load profile monitoring device 120a, 120b may include an absolute pressure sensor having a sensing diaphragm on one side and a sealed vacuum cavity on an opposing side.

In accordance with some embodiments of the present disclosure, load profile monitoring devices 120a, 120b may be integrally formed with the foot bed 106 of the lower-leg immobilizer 102 or other device. In other embodiments, the foot bed 106 may include a pocket and/or aperture into which the load profile monitoring devices 120a, 120b may be selectively located and/or fixed. Particularly in connection with embodiments in which the load profile monitoring devices 120a, 120b are separately formed and inserted into pockets or other structures, the load profile monitoring devices 120a, 120b may also be selectively removable and/or replaceable.

Figure 3A:
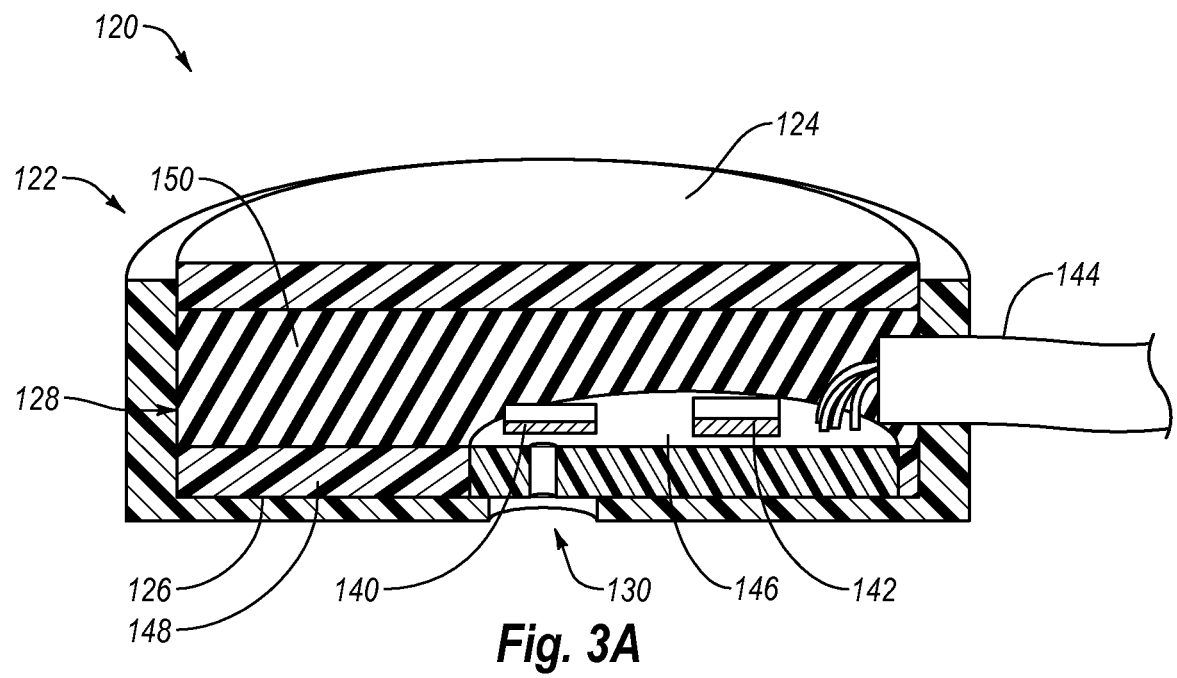
FIGS. 3A-3E illustrate cutaway perspective views of various example embodiments of load profile monitoring devices usable in connection with the systems of FIGS. 1 and 2.

Turning now to FIGS. 3A-3E, various example embodiments of load profile monitoring devices are illustrated and described in additional detail. FIG. 3A, for instance, illustrates a cutaway perspective view of one example embodiment of a load profile monitoring device 120. The load profile monitoring device 120 may include a housing 122. In some embodiments, the housing 122 of the load profile monitoring device 120 may be inserted into a pocket and/or aperture of a foot bed, such as foot bed 106 (see FIG. 2). In other embodiments, the housing 122 may be integrally formed, adjacent to, or otherwise oriented with respect to a foot bed or other structure.

As illustrated in FIG. 3A, the housing 122 may include a first surface 124 and a second surface 126. The first and second surfaces 124, 126 may cooperate to define at least a portion of a cavity 128. As shown in FIG. 3A, for instance, the first surface 124 may be an upper surface, while the second surface 126 may be a lower surface. In some embodiments, the first surface 124 may be a plate having interior and exterior sides. The cavity 128 can in some embodiments be defined by interior sides of both the first and second surfaces 124, 126 and thus be an interior cavity.

In accordance with some embodiments of the present disclosure, the first surface 124 may be sized and/or otherwise configured to be slidably received within the cavity 128. For instance, the first surface 124 and the cavity 128 may, in some embodiments, define a piston and cylinder configuration in which the first surface 124 is movable relative to the cavity 128, the housing 122, and/or the second surface 126. While the first surface 124 and the cavity 128 are represented as cooperating to define a cylindrical structure, such structure is merely exemplary. In other embodiments, the first surface 124 and the cavity 128 may be otherwise shaped. For example, the first surface 124 and the cavity 128 may define a structure having a polygonal, spherical, hemispherical, prismatic, or other configuration, or which has any combination of the foregoing structures.

At least to allow some movement of the first surface 124 relative to the cavity 128 and/or the housing 122, the first surface 124 may be flexibly connected to the second surface 126. For example, the first surface 124 may be connected to the second surface 126 by an elastomer, gel, other component, or a combination thereof. The connection between the first surface 124 and the second surface 126 may be formed by coating, bonding, integrally forming, other connection mechanisms, or combinations thereof. Optionally, connecting the first surface 124 with the second surface 126 may substantially seal the cavity 128 of the housing 122 to limit and/or prevent leakage and/or passage of contaminants.

The first surface 124 and/or the second surface 126 are optionally formed of a rigid material. For example, the first surface 124 and/or the second surface 126 may be formed of a rigid urethane. Example rigid urethanes may be castable, machineable, or can otherwise be shaped into a desired form. An example of a suitable material is Alumilite®, which is a rigid polymer that can be cast into a desired form. Other suitable materials include high-density polyethylene, polycarbonate, bakelite, duroplast, acrylic plastics, polybutylene terephthalate, polyethylene terephthalate, or any number of polymers, metals, composites, organic materials, or other materials, or any combination of the foregoing. In other embodiments, the first surface 124 and/or the second surface 126 may be pliable, flexible, or semi-rigid.

In the present embodiment, the first surface 124 and the second surface 126 are formed of the same material, and may have the same general properties (e.g., strength, stiffness, thermal expansion, etc.). In other embodiments, the first surface 124 and the second surface 126 may be formed of the same or different materials having substantially similar or different general properties. For example, one of the first or second surfaces 124, 126 may be formed of a flexible material while the other of the first or second surface 124, 126 may be formed of a rigid material. In another example, the first surface 124 may be formed of a first flexible material while the second surface 126 may be formed of a second flexible material.

The second surface 126 of the housing 122 may include an optional aperture 130 extending through at least a portion thereof. The aperture 130 may correspond to the apertures 116 described above in connection with FIG. 2, and the aperture 130 may have any number of uses. For instance, the aperture 130 may be used to facilitate obtaining of a reference pressure. In other embodiments, the aperture 130 may facilitate selective removal and/or replacement of components within the housing 122, or transmission or communication with sensing or conditioning elements within the load profile monitoring devices 120.

For instance, in one embodiment, the load profile monitoring device 120 may include a pressure sensor 140. The pressure sensor 140 may be configured to measure a load profile of the patient during a desired period of PWB, or for another treatment or purpose. In the present embodiment, the cavity 128 may be an interior cavity sized to receive all or a portion of the pressure sensor 140. For instance, in this particular embodiment, the cavity 128 has a substantially uniform height that may generally correspond to a distance between the first surface 124 and the second surface 126.

The height of the cavity 128 may be sufficient to allow the pressure sensor 140 to be positioned therein. For instance, in FIG. 3A, the pressure sensor 140 is wholly enclosed within the cavity 128, although in other embodiments the pressure sensor 140 may only be partially enclosed within the cavity 128, or may be external to the cavity 128. In still other embodiments, the cavity 128 may have a non-uniform height or other dimension.

The pressure sensor 140 of FIG. 3A may be in electronic communication with any number of other components. For instance, in this embodiment, the pressure sensor 140 is supported on a plate 146, and the plate 146 also supports a signal conditioner 142. The plate 146 may include, for instance, a printed circuit board or other signal communication mechanisms that can facilitate communication between the pressure sensor 140 and the at least one signal conditioner 142. Signal conditioners 142 may generally include amplifiers, filters, input/output ports, microchips, other signal conditioners, or combinations thereof.

The pressure sensor 140 may further include or be electronically coupled to an input/output 144. The input/output 144 may be configured to receive or otherwise obtain data generated by the pressure sensor 140. Such data may include, for instance, profile data related to loading of the load profile monitoring device 120, including pressures measured or otherwise monitored by the pressure sensor 140. The input/output 144 may include or be connected to a data acquisition or storage device and/or may be in electronic communication with at least one power source (not shown). A power source may include a battery power source, a direct power source, other power sources, or combinations thereof.

The pressure sensor 140 may take any suitable form. For instance, in at least one embodiment, the pressure sensor 140 may include a miniature piezoresistive Wheatstone bridge sensor. A Wheatstone bridge sensor may provide favorable mechanical properties. By way of illustration, a Wheatstone bridge sensor may provide high linearity, high strength, high mechanical repeatability, high stiffness, little to no hysteresis, repeated cycling until failure, reduced variability between other Wheatstone bridge sensors, other features, or combinations thereof. Furthermore, a Wheatstone bridge sensor may be capable of monitoring loads over an extended period of time. For example, the Wheatstone bridge sensor may be capable of monitoring loads over about a two week period of time.

Other types of pressure sensors or other devices may also be utilized. For instance, modified Wheatstone bridge sensors or other types of sensors may be used. Examples of some such devices include Carey Foster bridges, Kelvin Varley slides, Kelvin double bridges, Maxwell bridges, Murray loop bridges, Wein's bridges, Fiber Bragg gratings, or potentiometric, piezoelectric, electromagnetic, or capacitive pressure sensors, transducers or manometers. Furthermore, the manner in which pressure is measured may be varied based on the type of pressure sensor utilized. For instance, some pressure sensors may measure pressure relative to vacuum pressure or atmospheric pressure, as a differential pressure in the form of a pressure drop or gain relative to a reference pressure. For instance, in one embodiment an absolute pressure sensor may be used to measure a pressure relative to a vacuum within a void in the housing 122, or a reference pressure that is pre-calibrated with respect to the pressure sensor 140. Indeed, in some instances (see FIG. 3B), the pressure sensor 140 may not necessarily have access to atmospheric pressure. For instance, a pressure sensor may be sealed within a cavity of the housing 122 and pre-calibrated to measure pressure relative to sea level pressure or some other pressure. Such calibration of the pressure sensor may be performed prior to placing an initial placement of a load on the pressure sensor, such that calibration need not be performed subsequent beginning use of the pressure sensor in connection with a lower-leg immobilizer or other similar device.

With respect to use of a Wheatstone bridge or other sensor with high linearity, little to no hysteresis, reduced variability between sensors, or other features, or combinations thereof, such sensors may be desirable in order to reduce or eliminate the amount of calibration required for each sensor. In general, a sensor with high linearity, little to no hysteresis, reduced variability between sensors, or other features or combinations thereof may result in a more accurate sensor that may not require individual calibration, or may not require additional calibration following an initial calibration. Nevertheless, other sensors usable in connection with embodiments herein may have specific and/or repeated calibration requirements.

High strength, high mechanical repeatability (including repeated cycling until failure), and high stiffness in a pressure sensor may also be desirable in order to reduce and/or prevent breakage due to stresses, fatigue, or other loading issues. For example, pressure sensors that are subject to stresses, fatigue, vibrational loading, or other loading issues may experience wire breakage, damage to the device, or other problems that may affect the accuracy of the sensor.

The particular type of pressure sensor or load profile monitoring device used may vary in accordance with any number of different factors. For instance, as noted previously, in some embodiments there may be shock absorption features used in connection with a lower-leg immobilizer that makes use of a pressure sensor or other load profile monitoring device. In some such cases, such shock absorption features may affect the monitoring or degree of the load profile monitored by a load profile monitoring device. Accordingly, a load profile monitoring devices may be chosen to optimize use with a particular shock absorption feature. For instance, a particular type of pressure sensor may be less prone to the effects of a particular type of shock absorption feature. Alternatively, another type of pressure sensor may be adjustable so as to compensate for effects of the shock absorption features.

Although at least one of the various mechanical or other properties described above may be desirable, these mechanical properties are not intended to limit the scope of the present disclosure. Rather, the claims must be used to determine the proper scope of the disclosure. In other words, in order to fall within the scope of the claims a pressure sensor need not provide any of the mechanical properties described above.

In some embodiments, the pressure sensor 140, signal conditioner 142, plate 146, and input/output 144, or a portion thereof, may be sealed together in an integral unit. For instance, after securing the pressure sensor 140, signal conditioner 142, input/output 144, or other components to the plate 146, a polymer coating may be applied to connect such components together. Any other suitable type of coating or shell may also be used.

As also illustrated in FIG. 3A, the pressure sensor 140 may at least partially encapsulated by, or generally in contact with, a force transmitter 150. In accordance with some example embodiments, the pressure sensor 140 may directly, or indirectly via the plate 146, abut the second surface 126 of the housing 122 such that an upper surface of the pressure sensor 140 is encapsulated by, generally disposed within, or at least proximate, the force transmitter 150. In another embodiment such as that depicted in FIG. 3A, the pressure sensor 140 may be substantially fixed relative to the housing 122. For instance, in this embodiment, the pressure sensor 140 is supported on a plate 146 or other support which abuts the second surface 126. A brace member 148 may also abut or otherwise be adjacent the second surface 126. The brace member 148 may further engage the plate 146 and/or otherwise provide a support which maintains the plate 146 at a desired location. For instance, where the cavity 128 has a circular cross-sectional shape, the brace member 148 may be sized and shaped to fit within the cavity 128, and can optionally be dimensioned to be approximately the same size as the cavity 128. An opening, hole, slot, or other structure can be formed in the brace member 148, and the plate 146 can be received therein. The brace member 148 may also be structured in other manners, or even eliminated. For instance, an adhesive, mechanical fastener, or other device may secure the plate 146 in a desired location. Alternatively, as discussed hereafter, the brace member 148 and/or pressure sensor 140 may be movable within the housing 122.

In some embodiments it is nonetheless desirable to fix the location of the plate 146 and/or the pressure sensor 140. For instance, as shown in FIG. 3A, the pressure sensor 140 may be exposed to atmospheric pressure via the aperture 130. The aperture 130 can align with the illustrated opening in the plate 146, as well as with reference holes 116 (see FIG. 2). Such alignment may allow provision of atmospheric or another pressure to the pressure sensor 140, for use as a reference pressure. Fixing the location of the plate 146 and/or pressure sensor 140 can facilitate maintenance of alignment between with the aperture 130. In other embodiments, the plate 146 and/or the pressure sensor 140 may be movable. For instance, the reference pressure may be a gauge or relative pressure not utilizing atmospheric pressure. Indeed, a reference pressure may include a pressure measured by the pressure sensor 140 within the housing 122. In at least such cases, the pressure sensor 140 and/or plate 146 may be movable so as to change location, orientation, or other configuration within the cavity 128.

The force transmitter 150 may be structured to transmit a force received from the first surface 124, and can include any number of different configurations, materials, or the like. For instance, in accordance with some embodiments, the force transmitter 150 may include a fluid or gel that may be selected to transmit pressure from the first surface 124 and/or second surface 126 to the pressure sensor 140. Optionally, that fluid or gel may be substantially incompressible. As a result, as a force is applied to the force transmitter 150, the gel or fluid may experience minimal or no compression, and may instead develop a pressure therein, with the pressure being related to the applied load. Alternatively, the force transmitter 150 may be some other incompressible or substantially incompressible material, including a solid material, biasing mechanism, or other material, or any combination of the foregoing.

The compressibility of the force transmitter 150 may affect the uniformity of the transmission of forces to the pressure sensor 140. However, a compressible material may be acceptable in some situations for a force transmitter 150. For example, a minimally compressible material may still transmit forces to the pressure sensor 140, albeit non-uniformly in some circumstances. Examples of an acceptable fluid or gel for a force transmitter 150 may include a non-compressible silicone gel, other gels, other fluids, or combinations thereof.

During manufacture of the load profile measuring device, the force transmitter 150 may be positioned within the cavity 128. Thereafter, a vacuum or other pressure may be applied the cavity 128. In applying a vacuum to the cavity 128, it may be possible to remove other undesired materials (e.g., particles, gases, residues) from within the inner cavity 128. Additionally, applying a vacuum to cavity 128 may also provide a vacuum pressure within cavity 128 that may be used as a reference pressure for the pressure sensor 140. Application of a vacuum pressure, or other manufacturing processes may further be used to limit or prevent later introduction of other materials that may affect the uniformity of compression of the force transmitter 150 or the transfer of force from the force transmitter 150 to the pressure sensor 140.

While FIG. 3A therefore generally illustrates a load profile monitoring device 120 in which a housing 122 includes a movable upper surface or plate 124, and in which a non-compressible fluid 150 and pressure sensor 140 are disposed within the cavity 128, it should be appreciated that the embodiment of FIG. 3A is merely illustrative. For instance, although the pressure sensor 140 and/or signal conditioner 142 are illustrated as being on a plate 146 abutting the lower, second surface 126 of the housing 122, such is not intended as a limiting aspect of the present disclosure. For instance, in other embodiments, the pressure sensor 140 and/or signal conditioner 142, or a plate attached thereto, may abut the upper, first surface 124 of the housing, may be disposed entirely or partially within the force transmitter 150, may be oriented in a manner that is non-parallel to the first or second surfaces 224, 226, or may be generally proximate the first or second surface 124, 126 without abutting such surfaces. Moreover, the brace member 148 may also be eliminated or modified (e.g., to allow the plate 146 to move freely within cavity 128).

Figure 3B:
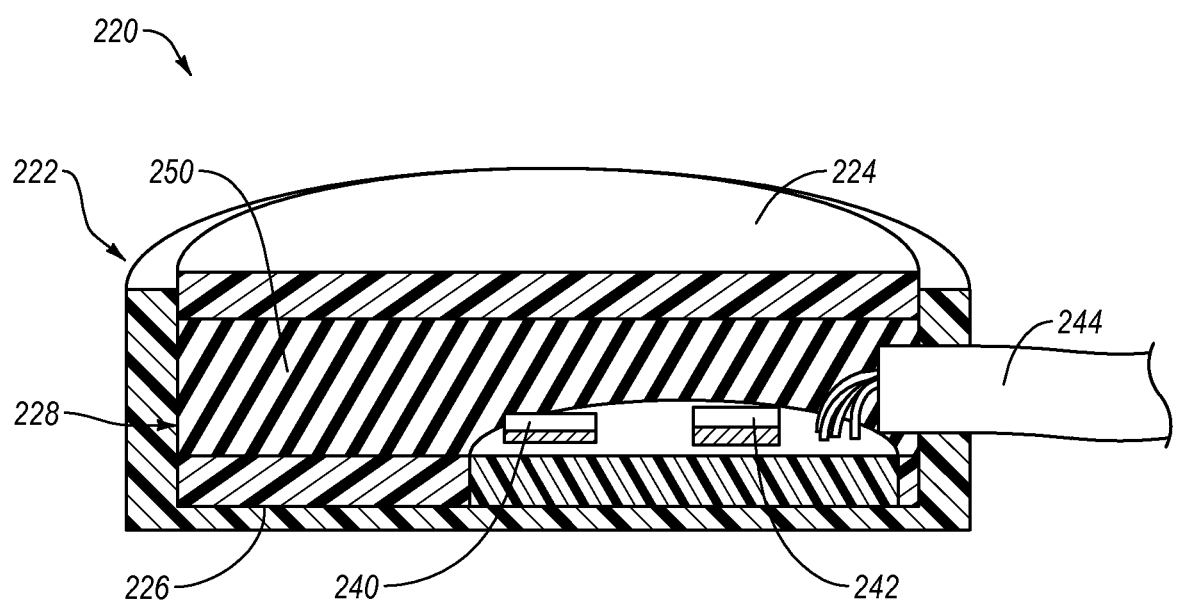

Turning now to FIG. 3B another example embodiment of a load profile monitoring device 220 is illustrated in additional detail. In general, the load profile monitoring device 220 is similar in various regards to the load profile monitoring device 120 described above with reference to FIG. 3A. Accordingly, to avoid obscuring certain aspects of the illustrated embodiment, a full detail of all aspects of the present embodiment may not be repeated, but may be understood by reference to the disclosure herein.

In FIG. 3B, the load profile monitoring device 220 includes a housing 222 in which a lower surface of an upper plate 224 and an interior, bottom surface 226 of the housing 222 define a cavity 228. The terms upper, lower, interior, and bottom are merely provided as relative terms based on the orientation illustrated in FIG. 3B; however, it should be appreciated that such relative terms are not necessarily limiting of the present disclosure as the load profile monitoring device 220 may be oriented in any number of different manners.

The housing 222 may define a piston and cylinder configuration in which the upper plate 224 may be configured to be at least partially movable relative to the cavity 228 and/or the bottom surface 226. For instance, as a compressive force is placed on the upper surface of the plate 224, the plate 224 may tend to move towards the lower surface 226, which may also change a size of the cavity 228. In some embodiments, a force transmitter 250 may also receive a force and exert a force on the lower surface of the plate 224, which force would tend to move the upper plate in a direction increasing a size of the cavity 228. The force exerted by the force transmitter 250 may be about equal and opposite that of the compressive force applied to the upper plate. The force transmitter 250 may, for instance, be substantially non-compressible and thus fully or partially resist movement of the upper plate 224 when a compressive force is applied thereto.

More particularly, the force transmitter 250 may be placed or otherwise located within the cavity 228. The force transmitter 250 may be similar to those described elsewhere herein. Thus, according to some embodiments, the force transmitter 250 may include a substantially non-compressible material such as a fluid, gel, elastomer, or the like. In still other embodiments, the force transmitter 250 may be at least partially compressible. The force transmitter 250 may also fill all or substantially all of the cavity 228. As a result, when the volume of the cavity 228 is about equal to the volume of the force transmitter 250, the force transmitter 250 may fully or partially resist a downward, or compressive force applied to the upper plate 224.

As the compressive force is placed on the upper surface of the plate 224, the force may be transmitted as a pressure into the force transmitter 250. More particularly, as noted above, the force may compress, or attempt to compress, the force transmitter 250. As shown in FIG. 3B, a pressure sensor 240 and signal conditioner 240 may be disposed on a plate or other support. In this embodiment, the pressure sensor 240 may be supported in a manner that is generally parallel to the upper plate 224 and the surface 226. As a result, the pressure sensor 240 may also be generally in-line with the force exerted on the force transmitter 250 by the upper plate 224. More particularly, a pressure is formed within the force transmitter 250 as a result of the force on the upper plate 224, and the pressure sensor 240 may monitor such pressure and any changes thereto. The pressure sensor 240 may therefore monitor a load profile within the housing 222 or cavity 228, and can pass information to or through one or more of the signal conditioner 242 and an input/output 244.

In the illustrated embodiment, the lower surface 226 of the housing 222 is shown as being substantially impermeable. Such a construction may be contrasted with the embodiment in FIG. 3A in which an aperture is formed in the lower surface of a housing. As discussed previously, a pressure sensor in accordance with aspects of the present disclosure may take any number of forms. Thus, while an atmospheric pressure may be obtained in some embodiments (e.g., through an aperture exposing a pressure sensor to the environment), in other embodiments a pressure measurement may be made in other manners, such as by referencing a different pressure. For instance, in the embodiment in FIG. 3B, a reference pressure may be pre-calibrated relative to the pressure sensor 240, such that a differential pressure relative to the reference or gauge pressure may be monitored.

Figure 3C:
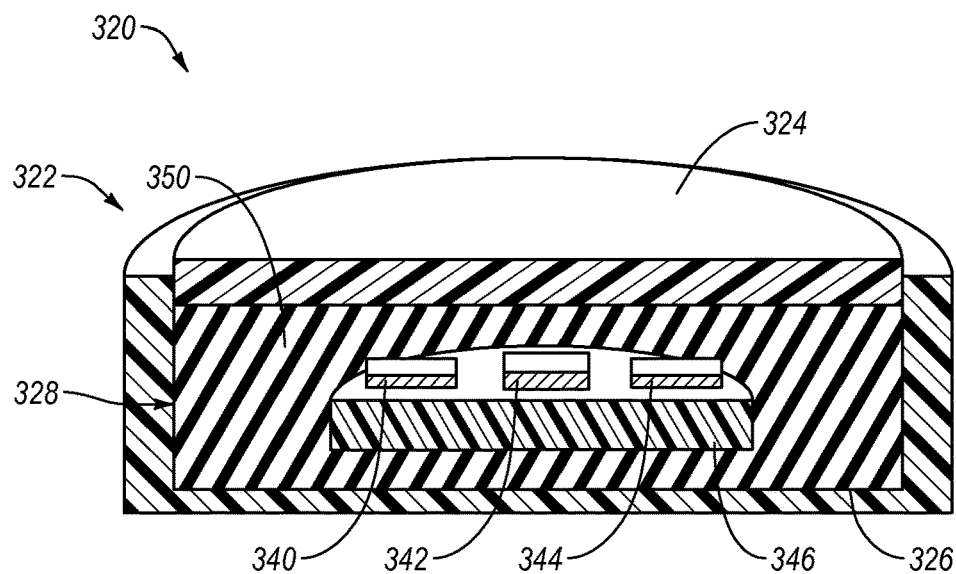

FIG. 3C illustrates still another exemplary embodiment of a load profile monitoring device 320 in accordance with some embodiments of the present disclosure. In the illustrated embodiment, the load profile monitoring device 320 includes a housing 322 defined at least partially by a first surface 324, and a second surface 326. In this embodiment, the first surface 324 generally takes the form of an upper plate while the second surface 326 takes the form of a lower or base plate. A cavity 328 may be defined within the housing 322, and may particularly have a size in at least one dimension that is generally related to a distance between the first and second surfaces 324, 326. As shown in FIG. 3C, a force transmitter 350 may be positioned at least partially within the cavity 328.

In the illustrated embodiment, a load profile may be monitored from within the force transmitter 350. More particularly, in at least some embodiments, a pressure sensor 340 can be fully encapsulated within the force transmitter 350. For instance, a pressure sensor 340 may be supported on a support 346, and the support plate 346 and pressure sensor 340 may be wholly internal to, or encapsulated by the force transmitter 350. Where the force transmitter 350 is a fluid, gel, or other similar material, the pressure sensor 340 and force transmitter 350 optionally are able to float or otherwise move within the force transmitter 350 to change location and/or orientation.

As a load is placed on the first surface 324, the load can be transferred to the force transmitter 350. In receiving the load, a pressure related to that load can be distributed through the force transmitter 350. The pressure sensor 340 may be in contact with the force transmitter 350 to monitor such pressure and the changes thereto. When the pressure sensor 340 monitors the pressure within the force transmitter 350, the measured or other monitored information can be provided to a signal conditioner 342 and/or an input/output 344. In some embodiments, the signal conditioner 342 and/or the input/output 344 are fully encapsulated within the force transmitter 350. In other embodiments, the pressure sensor 340, support 346, signal conditioner 342, input/output 344, or any combination of the foregoing are partially encapsulated within the force transmitter 350.

The pressure sensor 340 may include or be electronically coupled to the input/output 344. The input/output 344 may be configured to receive or otherwise obtain data generated by the pressure sensor 340, which data may include, for instance, profile data related to loading of the load profile monitoring device 320, including pressures measured or otherwise monitored by the pressure sensor 340. The input/output 344 may include or be connected to a data acquisition or storage device and/or may be in electronic communication with at least one power source (not shown). A power source may include a battery power source, a direct power source, other power sources, or combinations thereof. The data acquisition or storage device, or the power source, may be internal to the input/output 344, or separate therefrom. For instance, in some embodiments, the input/output 344 may be a device capable of wireless transmission. A power source may be included in the input/output as may a wireless transmitter. In such an embodiment, information can be transferred wirelessly from to a data acquisition or storage device outside the force transmitter 350 and/or the cavity 328.

Figure 3D:
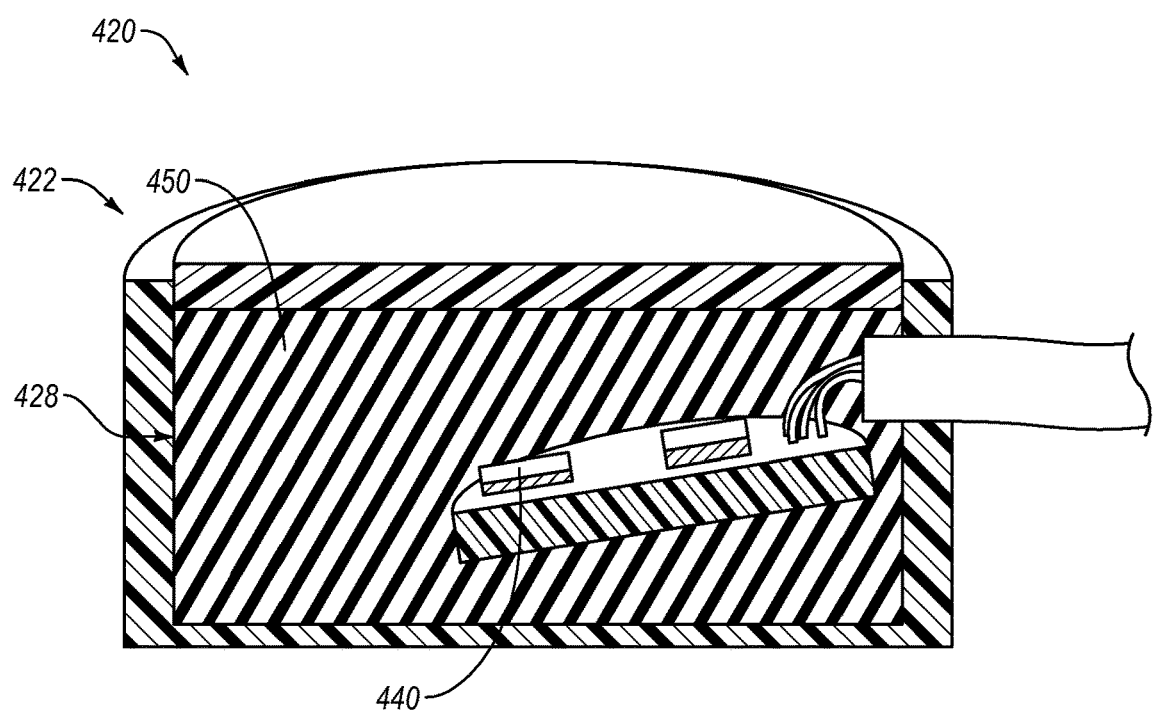

FIG. 3D illustrates an embodiment of a load profile monitoring device 420 similar to that disclosed above with respect to FIG. 3C. For instance, a housing 422 defines a cavity 428, in which a force transmitter 450 is located. The force transmitter 450 may be capable of transmitting a force as a pressure. By way of illustration, a force on the housing 422 may result in a pressure build-up within the force transmitter 450. A pressure sensor 440 may be encapsulated within the force transmitter 450 in a manner that allows the pressure sensor 440 to measure changes to the pressure that build-ups within the force transmitter 450.

In one embodiment, the pressure in the force transmitter 450 is omnidirectional. By way of illustration, the force transmitter 450 may include a substantially non-compressible gel. As pressure builds-up in the gel, the pressure throughout the gel may be substantially constant, regardless of the location or orientation from which a measurement is made. As a result, pressure may be monitored from any direction, and regardless of the orientation of a pressure sensing device. Accordingly, in FIG. 3D, the load profile monitoring device 420 may include a pressure sensor 440 and/or signal conditioner 442 which are optionally supported on a plate or other support, and are configured to monitor pressure in a direction that is offset from the line-of-action of the force applied to the housing 422. By way of illustration, the load profile monitoring device 120 of FIG. 3A may include a pressure sensor 140 that is optionally stabilized to be oriented in a single direction that is out of alignment with the line-of-action of an applied force. Alternatively, the pressure sensor 140 may be generally aligned with the line-of-action. In still other embodiments, the pressure sensor 440 of FIG. 3D may sometimes be offset from a line-of-action in which a force is applied to the housing 422. For instance, the pressure sensor 440 may be free to float, move, or otherwise change position, orientation, or other configuration, or any combination of the foregoing, while within the cavity 428, and even while encapsulated within the force transmitter 450. The pressure sensor 440 may therefore monitor a pressure even when out of alignment with a line-of-action of the applied force. Further still, the pressure sensor 440 may receive a pressure from the force transmitter 450 and by virtue of being within the force transmitter 450, transmit the pressure to the force transmitter 450.

Figure 3E:
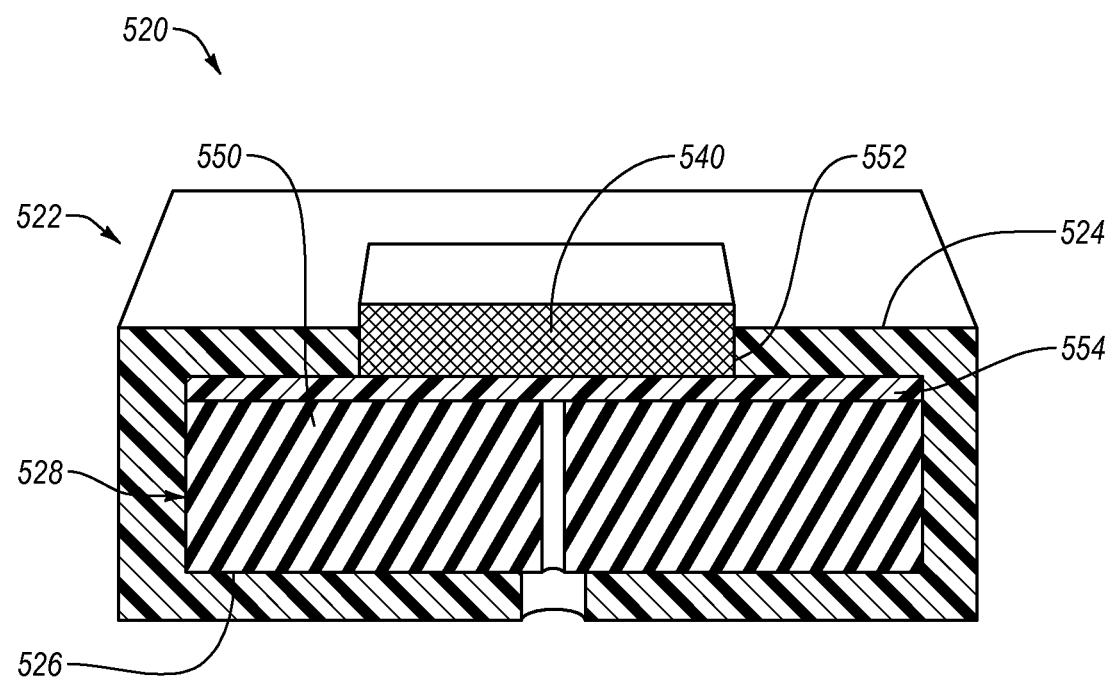

Still another example embodiment of a load profile monitoring device 520 is illustrated in FIG. 3E. In particular, in the illustrated embodiment, a housing 522 includes first and second surfaces 524, 526 which at least partially define an interior cavity 528 of the housing 522. A force transmitter 550 is positioned within the cavity 528.

In some embodiments, the first and second surfaces 524, 526 may be fixed relative to each other; however, in other embodiments, one or more of the first and second surfaces 524, 526 may be movable relative to each other. For instance, the first surface 524 could be slideably disposed relative to the housing so as to create a piston and cylinder configuration. In the illustrated embodiment however, the first and second surfaces 524, 526 are fixed. In this embodiment, rather than moving all or substantially all of an upper first surface 524 of the housing 522, an aperture 552 is formed in the first surface 524. Positioned within the aperture 552 is a movable element 540. The movable element 540 may be configured to slide or otherwise move relative to the first surface 524 and/or the second surface 526. In some embodiments, a flexible membrane may be attached to the movable element 540 and the housing 522 to allow the movable element 540 to move within the aperture 552 in the first surface while also maintaining the movable element 540 flexibly secured to the housing 522.

A load may also be applied to the movable element 540. For instance, the load profile monitoring device 520 may be used in connection with a lower-leg immobilizer and, as the patient walks or otherwise puts his or her weight on the immobilized foot, the force may be exerted on the movable element 540 in the form of a load. The movable element 540 may then exert a compressive force on the force transmitter 550, which can optionally cause a pressure to build within the force transmitter 550.

In at least some embodiments, the movable element 540 is a pressure sensor, includes a pressure sensor, or is coupled to a pressure sensor or similar device. Accordingly, in some embodiments, the force placed on the movable element 540 may be measured directly. In other embodiments, a pressure sensor may be disposed within or adjacent the force transmitter 550 so as to obtain a pressure reading when a load is placed on the movable element 540. For instance, a pressure sensor may be disposed within or proximate the force transmitter 550 in a manner similar to those described above with reference to FIGS. 3A-3D. Furthermore, while the movable element 540 may transfer a compressive force directly to the force transmitter 550, such an embodiment is merely exemplary. For instance, in FIG. 3E, a force distribution member 554 may be positioned between at least a portion of the movable element 540 and the force transmitter 550. The force distribution member 554 can have a surface area greater than that of the movable element 540, and potentially about as large as a footprint of the cavity 528. Thus, as the movable element 540 exerts a compressive force on the force distribution member 554, the force distribution member 554 can potentially move within the cavity 528, and may further distribute the load over a larger area, thereby more uniformly applying a pressure to the force transmitter 550.

Figure 4:
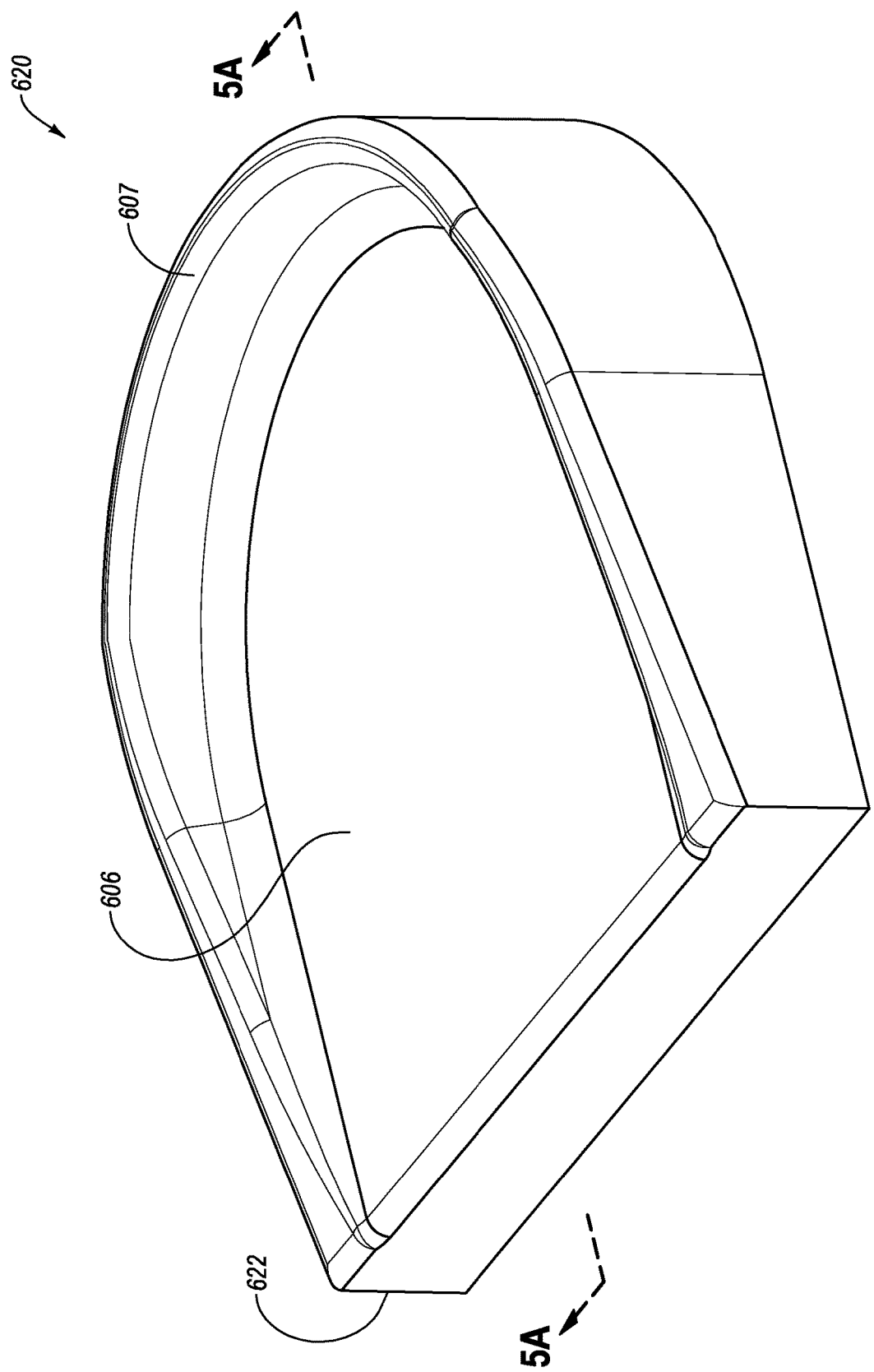
FIG. 4 illustrates a perspective view of a load profile monitoring device configured as a insole insert.

Attention is now directed to FIG. 4, which illustrates a load profile monitoring device 620 for use in measuring an under foot profile of a patient during a period of PWB. As shown in FIG. 4, the load profile monitoring device 620 includes a housing 622 configured as an insole insert that may be selectively placed in footwear worn during a period of PWB. More specifically, the housing 622 may be sized and shaped to fit within a patient's footwear (e.g. any ankle foot orthosis, a hard or other cast boot, a camwalker, walking boot cast, hard sole shoe, cast shoe, or a patient's regular footwear). As is common with insole inserts, the insole insert configured housing 622 may be selectively placed in or removed from the patient's footwear. Alternatively, the insole insert configured housing 622 may be configured for permanent placement within the patient's footwear.

The housing 622 may include a heel bed 606 and a heel ridge 607. When the housing 622 is placed in the patient's footwear, the patient's heel may be supported upon, and optionally oriented with respect to, the heel bed 606. Accordingly, in some embodiments the heel bed 606 may be sized, shaped, contoured, or otherwise configured to allow a patient to comfortably support his or her heel thereon. The heel ridge 607 may extend around at least a portion of the heel bed 606 to, for example, facilitate proper positioning of the patient's heel on the heel bed 606 and/or increase the comfort of the housing 622 when the patient's heel rests thereon. Furthermore, the housing 622 may be oversized or otherwise configured in some embodiments so as to accommodate more or the entirety of the patient's foot. In other words, the housing may be sized and shaped so that the heel bed 606 takes the form a foot bed upon which all or a portion of the patient's foot may be supported. Furthermore, the housing 622 may be sized to accommodate feet of different sizes, although the housing 622 may also be customized for a particular patient or foot size.

Figure 5A:
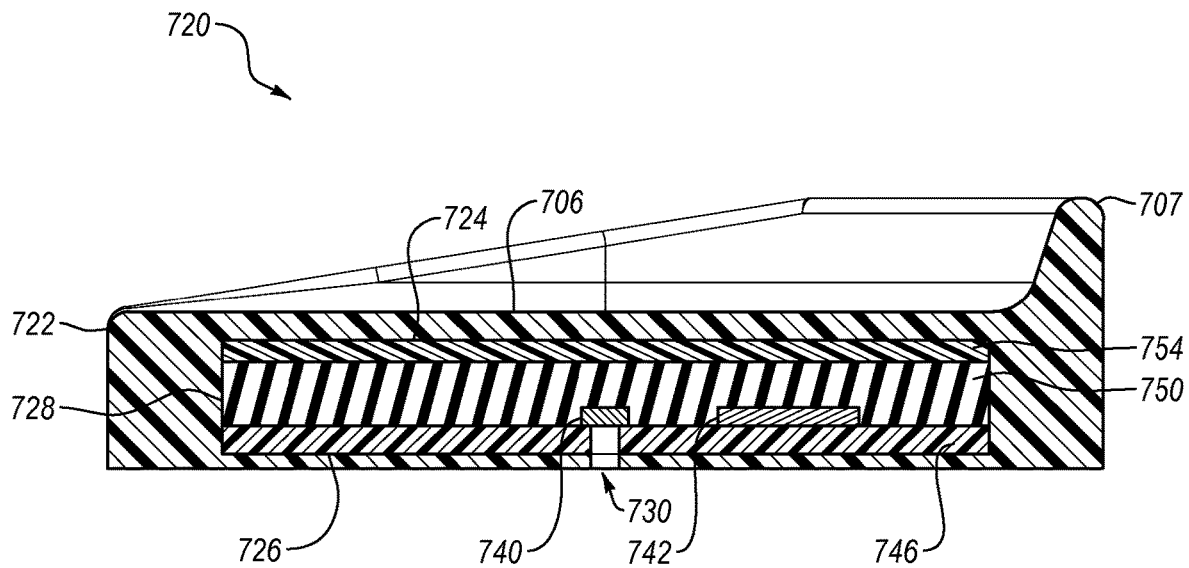
FIGS. 5A-5B illustrate cross-sectional views of various example embodiments of load profile monitoring devices configured as insole inserts similar to the device shown in FIG. 4.
Figure 5B:
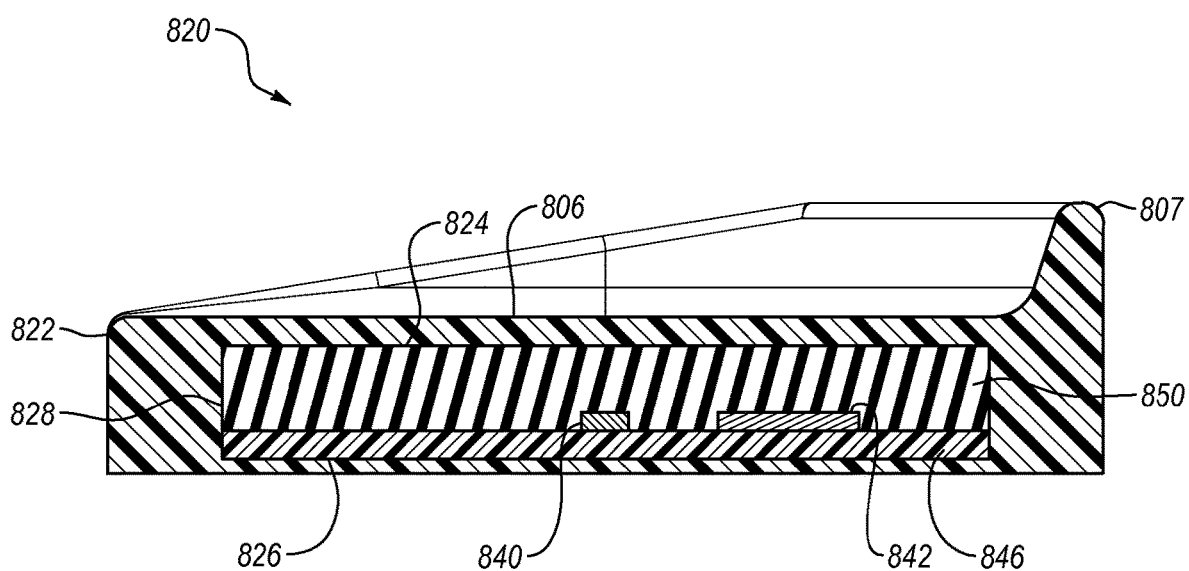

In order to use an insole insert configured load profile monitoring device, such as device 620, to measure, analyze, store, or otherwise monitor a load profile of a PWB patient, the load profile monitoring device may include various features, structures, or elements that perform one or more of these functions. FIGS. 5A and 5B illustrate example embodiments of insole insert configured load profile monitoring devices. In general, the load profile monitoring devices of FIGS. 5A and 5B are similar in various regards to the load profile monitoring devices described above with reference to FIGS. 3A-3E. Accordingly, to avoid obscuring certain aspects of the illustrated embodiment, a full detail of all aspects of the present embodiment may not be repeated, but may be understood by reference to the disclosure herein.

FIG. 5A, for instance, illustrates a cross-sectional view of one example embodiment of an insole insert configured load profile monitoring device 720. The load profile monitoring device 720 may include a housing 722. In the illustrated embodiment, the housing 722 of the load profile monitoring device 720 is shaped and configured as an insole insert that may be selectively or permanently placed in a patient's footwear. The housing 722 includes a heel bed 706 and a heel ridge 707, similar to heel bed 606 and heel ridge 607 discussed above.

As illustrated in FIG. 5A, the housing 722 may include a first surface 724 and a second surface 726. The first and second surfaces 724, 726 may cooperate to define at least a portion of a cavity 728. As shown in FIG. 5A, for instance, the first surface 724 may be an upper surface, while the second surface 726 may be a lower surface. An upper plate or force distribution member 754 may be disposed within the cavity 728 adjacent the first surface 724. Similarly, a lower plate 746 may be disposed within the cavity 728 adjacent the second surface 726.

In accordance with some embodiments of the present disclosure, the upper plate 754 may be sized and/or otherwise configured to be slidably disposed within the cavity 728. For instance, the upper plate 754 and the cavity 128 may, in some embodiments, define a piston and cylinder configuration in which the upper plate 754 is movable relative to the cavity 728, the housing 722, the lower plate 746, and/or the second surface 726. The upper plate 754 and/or the lower plate 746 may optionally be formed of a generally rigid material. In other embodiments, the upper plate 754 and/or the lower plate 746 may be pliable, flexible, or semi-rigid.

In some embodiment, the upper plate 754 and the lower plate 746 are formed of the same material, and may have the same general properties (e.g., strength, stiffness, thermal expansion, etc.). In other embodiments, the upper plate 754 and the lower plate 746 may be formed of the same or different materials having substantially similar or different general properties. For example, one of the upper or lower plates 754, 746 may be formed of a flexible material while the other of the upper or lower plates 754, 746 may be formed of a rigid material.

The second surface 726 of the housing 722 and/or the lower plate 746 may include an optional aperture 730 extending therethrough. Similar to the aperture 130 discussed above, the aperture 730 may have any number of uses. For instance, the aperture 730 may be used to facilitate obtaining of a reference pressure, such as atmospheric pressure. In other embodiments, the aperture 730 may facilitate selective removal and/or replacement of components within the housing 722, or transmission or communication with sensing or conditioning elements within the load profile monitoring devices 720.

For instance, in one embodiment, the load profile monitoring device 720 may include a pressure sensor 740. The pressure sensor 740 may be configured to measure a load profile of the patient during a desired period of PWB, or for another treatment or purpose. In the present embodiment, the cavity 728 may be an interior cavity sized to receive all or a portion of the pressure sensor 740. For instance, in this particular embodiment, the cavity 728 has a substantially uniform height that may generally correspond to a distance between the first surface 724 and the second surface 726. The height of the cavity 728 may be sufficient to allow the pressure sensor 740 to be positioned therein. For instance, in FIG. 5A, the pressure sensor 740 is wholly enclosed within the cavity 728, although in other embodiments the pressure sensor 740 may only be partially enclosed within the cavity 728, or may be external to the cavity 728. In still other embodiments, the cavity 728 may have a non-uniform height or other dimension.

The pressure sensor 740 of FIG. 5A may be in electronic communication with any number of other components. For instance, in this embodiment, the pressure sensor 740 is supported on lower plate 746, and the lower plate 746 also optionally supports a signal conditioner 742. The lower plate 146 may include, for instance, a printed circuit board or other signal communication mechanisms that can facilitate communication between the pressure sensor 740 and the at least one signal conditioner 742. Signal conditioners 742 may generally include amplifiers, filters, input/output ports, microchips, other signal conditioners, or combinations thereof.

Although not shown in FIG. 5A, the pressure sensor 740 may further include or be electronically coupled to an input/output similar to the input/output 144 discussed above. Furthermore, the pressure sensor 740 may take any suitable form, as discussed elsewhere herein. For instance, the pressure sensor 740 may include a miniature piezoresistive Wheatstone bridge sensor, modified Wheatstone bridge sensors, Carey Foster bridges, Kelvin Varley slides, Kelvin double bridges, Maxwell bridges, Murray loop bridges, Wein's bridges, Fiber Bragg gratings, or potentiometric, piezoelectric, electromagnetic, or capacitive pressure sensors, transducers or manometers.

As also discussed herein, the manner in which pressure is measured may be varied based on the type of pressure sensor utilized. For instance, as discussed herein, some pressure sensors measure pressure relative to vacuum pressure or atmospheric pressure, as a differential pressure in the form of a pressure drop or gain relative to a reference pressure, or based on a gauge pressure. When a sensor is used that measures pressure relative to atmospheric pressure, the aperture 730 may be included to expose the sensor to atmospheric pressure, thereby allowing the sensor to use atmospheric pressure as a reference pressure.

As also illustrated in FIG. 5A, the pressure sensor 740 may be at least partially encapsulated by, or generally in contact with, a force transmitter 750. In accordance with some example embodiments, the pressure sensor 740 may directly, or indirectly via the lower plate 746, abut the second surface 726 of the housing 722 such that an upper surface of the pressure sensor 740 is encapsulated by, generally disposed within, or at least proximate, the force transmitter 750.

In the embodiment depicted in FIG. 5A, the pressure sensor 740 is substantially fixed relative to the housing 722. More specifically, the pressure sensor 740 is supported on the lower plate 746 which abuts the second surface 726. The lower plate 746 may be positioned within the cavity 728 so as to substantially remain in a desired location. For instance, the lower plate 746 may be sized and shaped to fit within the cavity 728, and can optionally be dimensioned to be approximately the same size as the cavity 728. Alternatively, a brace member, similar to brace member 148 discussed above, an adhesive, a mechanical fastener, or other device may be used to hold the lower plate 746 in the desired location.

In other embodiments, the lower plate 746 and/or the pressure sensor 740 may be movable. For instance, the reference pressure may be a gauge or relative pressure not utilizing atmospheric pressure. Indeed, a reference pressure may include a pressure measured by the pressure sensor 740 within the housing 722. In at least such cases, the pressure sensor 740 and/or the lower plate 746 may be movable so as to change location, orientation, or other configuration within the cavity 728, similar to the embodiments shown FIGS. 3C and 3D and described above.

Like the force transmitters discussed above, the force transmitter 750 may be structured to transmit a force received from the first surface 724 and/or the upper plate 754, and can include any number of different configurations, materials, or the like. For instance, in accordance with some embodiments, the force transmitter 750 may include a fluid or gel that may be selected to transmit pressure from the first surface 724, upper plate 754, lower plate 746, and/or second surface 726 to the pressure sensor 740. As a force is applied to the first surface 724 and/or the upper plate 754, the upper plate 754 may potentially move within the cavity 728 and, due to is relatively large surface area, may distribute the load over a larger area, thereby more uniformly applying a pressure to the force transmitter 750. The pressure sensor 740 may monitor the pressure applied to the force transmitter 750 to monitor the under foot load profile of the PWB patient.

Turning now to FIG. 5B, another example embodiment of a load profile monitoring device 820 is illustrated. In general, the load profile monitoring device 820 is similar in various regards to the load profile monitoring device 720 described above with reference to FIG. 5A. Accordingly, to avoid obscuring certain aspects of the illustrated embodiment, a full detail of all aspects of the present embodiment may not be repeated, but may be understood by reference to the disclosure herein.

In FIG. 5B, the load profile monitoring device 820 includes a housing 822 having a heel bed 806 and a heel ridge 807. The housing 822 also includes a first surface 824 and a second surface 826 that at least partially define a cavity 828. The first surface 824 and/or the second surface 826 may be configured to transfer a force applied thereto to a force transmitter 850 disposed within the cavity 828. The force transmitter 850 may be similar to those described elsewhere herein. Thus, according to some embodiments, the force transmitter 850 may include a substantially non-compressible material such as a fluid, gel, elastomer, or the like. In still other embodiments, the force transmitter 850 may be at least partially compressible. The force transmitter 850 may also fill all or substantially all of the cavity 828.

As the force is placed on the first surface 824 and/or the second surface 826, the force may be transmitted as a pressure into the force transmitter 850. More particularly, as noted above, the force may compress, or attempt to compress, the force transmitter 850. As shown in FIG. 5B, a pressure sensor 840 and signal conditioner 840 may be disposed on a plate 846 or other support. In this embodiment, the pressure sensor 840 is illustrated as being supported in a manner that is generally parallel to the first surface 824 and the second surface 826. As a result, the pressure sensor 840 may also be generally in-line with the force exerted on the force transmitter 850 by the first surface 824 and/or the second surface 826. More particularly, a pressure is formed within the force transmitter 850 as a result of the force on the first surface 824 and/or the second surface 826, and the pressure sensor 840 may monitor such pressure and any changes thereto. The pressure sensor 840 may therefore monitor a load profile within the housing 822 or cavity 828, and can pass information to or through one or more of signal conditioners 842 and an input/output (not shown).

In the illustrated embodiment, the second surface 826 of the housing 822 is shown as being substantially impermeable. Such a construction may be contrasted with the embodiment in FIG. 5A in which the aperture 730 is formed in the second surface 726 of housing 722. As discussed previously, a pressure sensor in accordance with aspects of the present disclosure may take any number of forms. Thus, while an atmospheric pressure may be obtained in some embodiments (e.g., through an aperture exposing a pressure sensor to the environment), in other embodiments a pressure measurement may be made in other manners, such as by referencing a different pressure. For instance, in the embodiment in FIG. 5B, a reference pressure may be pre-calibrated relative to the pressure sensor 840, such that a differential pressure relative to the reference or gauge pressure may be monitored.

In the illustrated embodiment, plate 846 is positions on or adjacent to second surface 826, and pressure sensor 840 is supported on plate 840. As a result, pressure sensor 840 is positioned adjacent to, in contact with, or is disposed partially within force transmitter 850. As discussed above in connection with FIGS. 3C and 3D, a load profile may be monitored from within the force transmitter 850. Thus, in at least some embodiments, the pressure sensor 840 can be fully encapsulated within the force transmitter 850. For instance, the pressure sensor may be supported on a support, and the support and pressure sensor may be wholly internal to, or encapsulated by the force transmitter, similar to FIGS. 3C and 3D. Where the force transmitter is a fluid, gel, or other similar material, the pressure sensor and force transmitter optionally are able to float or otherwise move within the force transmitter to change location and/or orientation.

As a load is placed on the first surface 824 or the second surface 826, the load can be transferred to the force transmitter 850. In receiving the load, a pressure related to that load can be distributed through the force transmitter 850. The pressure sensor 840 may be in contact with the force transmitter 850 to monitor such pressure and the changes thereto. When the pressure sensor 840 monitors the pressure within the force transmitter 850, the measured or other monitored information can be provided to the signal conditioner 842 and/or an input/output (not shown).

As discussed above, the pressure in the force transmitter may be omnidirectional. As a result, the build-up of pressure in the force transmitter may be substantially constant, regardless of the location or orientation from which a measurement is made. Accordingly, pressure may be monitored from any direction, and regardless of the orientation of the pressure sensing device. Thus, the pressure sensor may be configured to monitor pressure in a direction that is in line with or offset from the line-of-action of the force applied to the housing, as discussed above.

Figure 6:
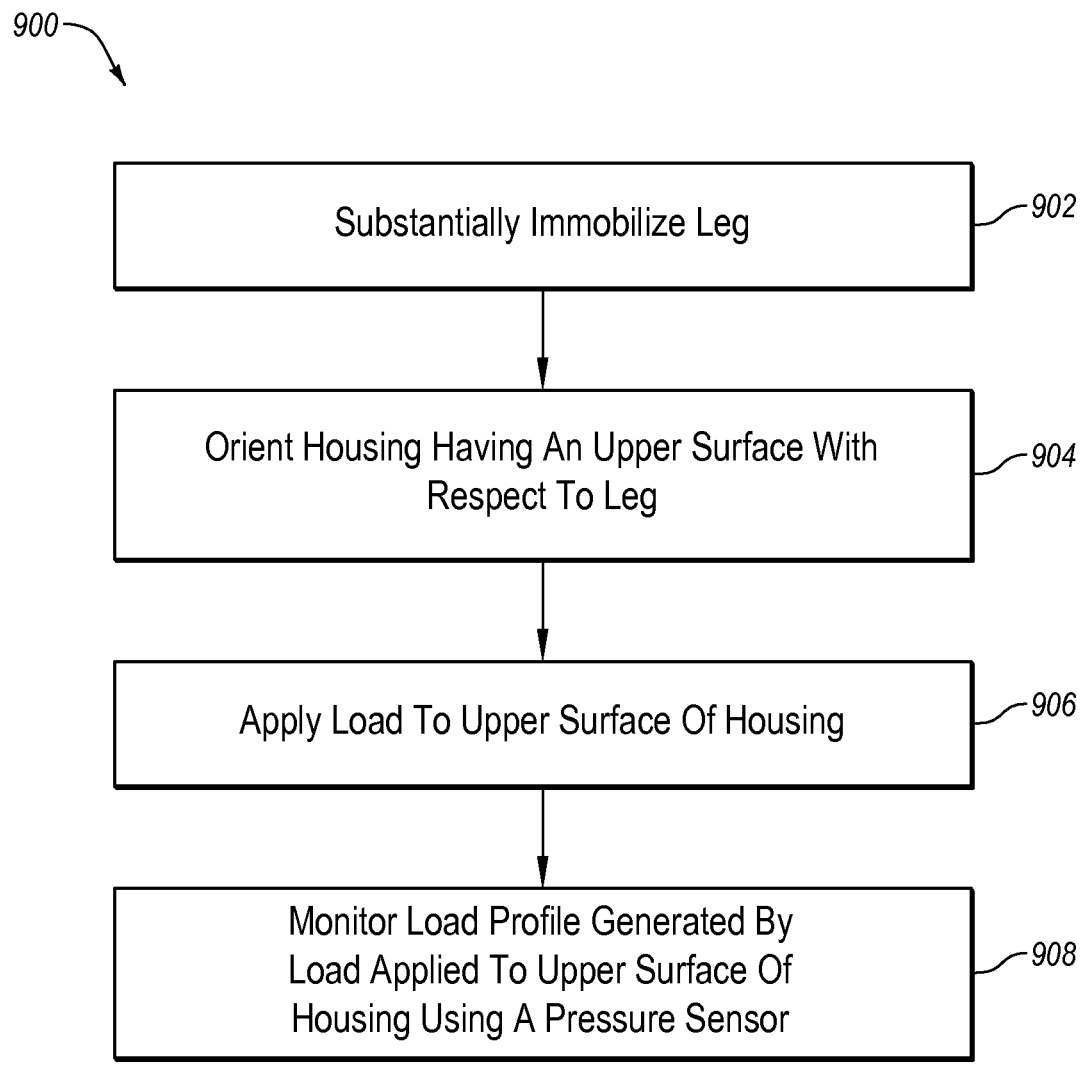
FIG. 6 illustrates an embodiment of a method for measuring an under foot load profile of a patient during a period of PWB.

FIG. 6 illustrates a method 900 for measuring an under foot load profile of a patient during a period of PWB. In this exemplary embodiment, the method includes substantially immobilizing a portion of the lower leg of a patient, as indicated by act 902. The lower leg may be immobilized by a lower-leg immobilizer including, but not limited to, a walking boot cast or the lower-leg immobilizer 100 described herein. As noted herein, other types of immobilizers may be used for different bone fractures. As also noted, some bone fractures may not require the use of an immobilizer. Accordingly, in the method, the step of immobilizing the lower leg may not be necessary.

The lower-leg immobilizer may include a housing, such as housing 122, that may be oriented, as indicated by act 904, with respect to the patient's lower leg. For example, the housing 122 may be positioned, for example, in a heel region and/or a ball region of the patient's foot when the fractured bone is the tibia.

A load may be applied to the load profile monitoring device, as indicated in act 906. More particularly, a load may be applied to an upper surface of the housing. For example, the patient may apply a load while standing, walking, sitting, or performing other activities. A load profile may be generated based on the applied load on the upper surface of the housing. For instance, a pressure sensor may be located fully or partially below the upper surface and at least partially within the housing. This generated load profile may be monitored, as indicated by act 908. For example, the generated load profile may be monitored over a two-week or a four-week period. The generated profile may be continuously monitored without substantial interruption. Alternatively, the generated load profile may be periodically monitored. For instance, a pressure sensor may be configured to activate, measure, or otherwise monitor a load only for a specified duration. The pressure sensor may then cease monitoring the load for a time and then again activate or otherwise monitor the load profile. Such a process may occur over regular or irregular intervals over a full period in which the load profile is monitored. In some embodiments, periodic monitoring may occur at specified times or intervals. In other embodiments, monitoring may be triggered by certain events (e.g., detection of a load or a high load on the lower-leg immobilizer).

The monitored load profile may be stored for later use. For example, a data acquisition unit may be used to store the monitored load profile. The data acquisition unit may be contained in the housing, in the lower-leg immobilizer, or in a remote location. The monitored load profile may be used to provide feedback to the patient. For example, the data acquisition unit may notify the patient when they have exceeded a prescribed PWB allowance. Direct feedback may improve the outcomes of a patient that has been prescribed PWB.

A user interface may be used with the monitored load profile. For example, the peak loads (e.g., a maximum load experienced during ambulation), an average load, or other data may be identified and presented to the user via an interface. The load profile information may be stored and/or used to provide direct feedback to the patient and/or clinician.

Monitoring the load profile may be performed without recalibration after first applying a load to the upper surface of the housing. For example, the pressure sensor may be configured to monitor the load profile without substantial drift.

The method 900 described above may also be used for treating a patient during a period of PWB. For example, the load profile data may be used to alter the initial PWB prescription. In other words, based on characteristics of the load profile, such as peak loads, cumulative loads, number of steps, other characteristics, or combinations thereof, the initial PWB prescription may be altered. In one example, for instance, a patient may have a load profile relative to an injury, such as a fractured bone, monitored during an extended period between check-ups. Upon detecting certain events or loads, the time between check-ups may be altered. For instance, upon determining that desired peak loads are being exceeded, a patient or physician may be automatically notified that a time between check-ups should be shortened. In contrast, if average loads fall within a desired range, or if peak loads are less than a set maximum, a patient or physician may be automatically notified that a time between check-ups should be extended. Other data related to a load profile may also be used to modify the time between check-ups and thus also a time during which a load profile is monitored.

WORKING EXAMPLES

An embodiment of a load sensor was configured as a piston and cylinder design similar to that illustrated in FIG. 3A, utilizing non-compressible silicone gel to generally uniformly transmit the pressure inside the cylinder to a piezoresistive Wheatstone bridge pressure sensor. In this example, the cylinder diameter remained substantially constant and the pressure measured by the piezoresistive sensor was converted to load.

One corner of a piezoresistive pressure sensor die (a gauge-type microsensor −3000 series 15 psi piezoresistive pressure sensor manufactured by Merit Sensors, Salt Lake City, USA) was secured to a custom FR-4 printed circuit board (Circuit Graphics, Salt Lake City, USA) using UV-cure adhesive (3311 Loctite, Henkel Co., Düsseldorf, Germany). The piezoresistive sensor was electrically connected to the printed circuit board by bonding aluminum-1% silicon alloy wire (Semiconductor Packaging Materials, Inc, Armonk, USA) between the pressure sensor die and the printed circuit board using a 7476 D Manual Wedge bonder (West bond, Anaheim, USA). Wire bonds were reinforced with a small amount of acrylic-based, UV-cure adhesive (3311 Loctite). The microsensor was further secured and sealed to the printed circuit board with a UV-cure silicone (5248, Loctite) around the remaining base perimeter. On the printed circuit board, the outputs of the piezoresistive sensor were connected to an AD8220 Instrumentation Amplifier (Analog Devices, Inc., Norword, USA) with a gain adjusting resistor, which was soldered to the printed circuit board. In a portion of the studies, the instrumentation amplifier was not used, in which case the output of the piezoresistive sensor was electrically connected directly to the output leads of the printed circuit board. To complete the circuitry, lead-out wires (AS 999-28-45J, Cooner Wires, Chatsworth, USA) were soldered to the printed circuit board.

The sensor housing and upper plate were fabricated from Alumilite® (Alumilite, Inc., Kalamazoo, USA), a two-part, rigid, castable urethane, poured into a silicone mold and allowed to cure for 5 minutes at room temperature. The assembled printed circuit board was placed on the bottom of the sensor housing, and atmospheric reference holes were provided and aligned. Alumilite® was poured into the sensor housing to seal the printed circuit board and leadout wires to the sensor housing. Silbione HS firm gel LV 10-1 (Bluestar Silicones, East Brunswick, USA) was mixed according to manufacturers specifications and de-gassed for 30 minutes. The de-gassed gel was poured into the sensor housing, vacuumed again, and then placed in a mechanical convection oven for 15 minutes at 125° C. to cure the gel. To seal the load sensor assembly, the upper plate was coated in VST-50 silicone elastomer, placed on top of the sensor assembly, and then placed in the oven for an additional 10 minutes to cure the elastomer.

Pressure Linearity Testing

Sensor sensitivity, linearity, and hysteresis were characterized on eight load sensors by applying known air pressures prior to and after the application of the gel, in order to assess the effects of the non-compressible silicone gel on the performance of the piezoresistive sensor. The eight tested load sensors were fabricated without amplifiers on the printed circuit board. Sensors were powered with 5V, and output voltages were recorded using a precision datalogger (34970 A, Data Acquisition System manufactured by Agilent Technologies, Santa Clara, USA). Pressure was applied to the load sensor assembly with an ER3000 digital pressure controller (Tescom, Elk River, USA). An airtight seal was created around the top of the load sensor assembly and the pressure incremented and decremented in 7 kPa (1 psi) steps from 0 to 210 kPa (30 psi). After the no-gel condition was tested, 5 grams of the Silbione HS Firm Gel was added to each load sensor and the pressure testing was repeated.

Custom MatLab (MathWorks, Natick, USA) programs were used to analyze data from both the 34970 A DAS and ER3000. The average value for each pressure increment for each sensor was calculated for both the input pressure and output voltage data. This data was used to calculate sensitivity, linearity and hysteresis. A Mann-Whitney U test for non-parametric data was used to determine statistical difference between the gel and non-gel condition for linearity.

The difference in sensitivities between the gel and no gel conditions were virtually undetectable using the described experimental setup. The measured sensitivity for both conditions and all eight sensors was about 0.0015 (SD 2.3×10-19) V/kPa. The average value of the correlation coefficient from the linear fit of the output voltage versus the input pressure graph for the no-gel and gel conditions were about 0.9998 (SD 3.5×10-4) and about 0.9999 (SD 8.3×10-5), respectively. A Mann-Whitney statistical test was used to compare the correlation coefficients between the gel and no-gel condition. There was virtually zero statistical difference between these conditions (P=0.774). FIG. 5 illustrates the results from one of the sensors evaluated during pressure linearity testing. There was no appreciable hysteresis between the loading and unloading curves. As there was no appreciable difference between sensor sensitivity and hysteresis, no further statistical analysis was performed.

Sensitivity Based Dimension Optimization

Nine different sensors assemblies of inner diameters of about 20, 26, and 34 mm and heights of about 6, 9, 12 mm were tested to evaluate the effect of the housing dimension on load sensor sensitivity. The sensors were supplied with a 5V input voltage (Agilent Technologies, Santa Clara, USA), and the output voltage was read with National Instruments PCI-6221 DAQ card with a custom Labview program (National Instruments, Austin, USA). Loading of the sample was performed with a compression testing instrument (model 3342—Instron, Norwood, USA). The sensor was incrementally loaded five times in steps of 15 N from 0 to 195 N. The raw data from the Instron and the DAQ were analyzed using Matlab and Excel. The average voltage output from the sensor for each load was graphed against the applied load. A linear regression was used to calculate the sensitivity.

The sensor housing dimensions were determined to have an effect on the sensitivity of the load sensor. The sensitivities ranged from about 0.0014 V/N with a housing diameter of about 34 mm to about 0.0164 V/N for a housing diameter of about 20 mm. While the housing diameter changed the sensor sensitivity by about 0.0063 V/N, the change in housing height had a less pronounced effect with an average change of about 0.0001 V/N. FIG. 6 displays the effects of varying diameter on load sensor sensitivity for three sensors with a sensor height of 9 mm.

Static Drift Testing

Figure 7:
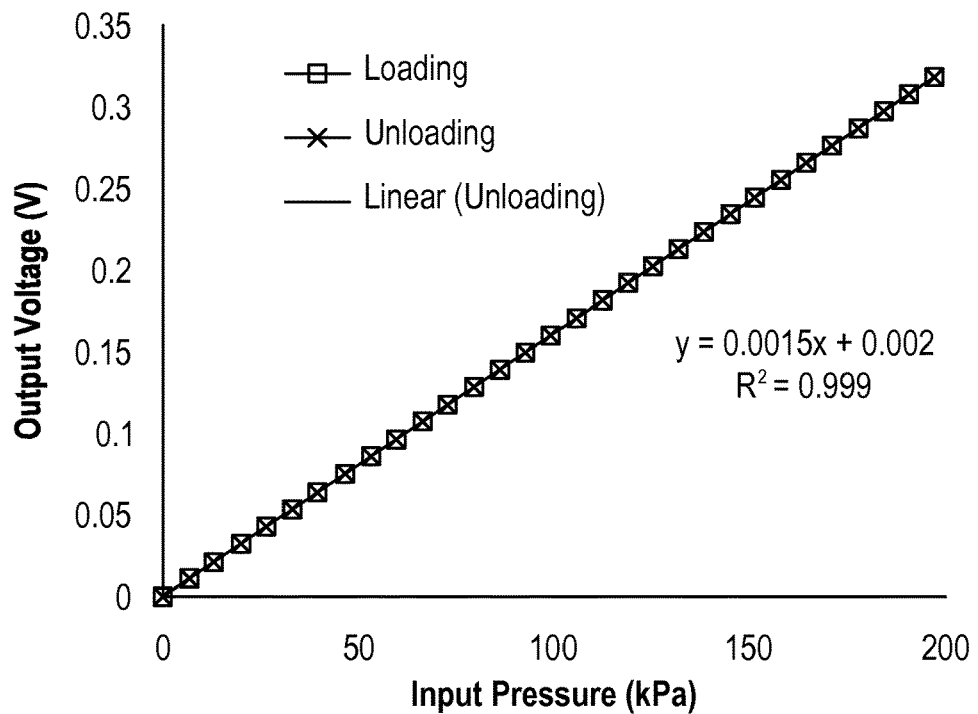
FIG. 7 illustrates the results from one of the sensors of a working example evaluated during pressure linearity testing.

The results of the sensitivity testing motivated the final dimensions of the sensor housing in one working example, although other suitable dimensions may be used. The inner diameter was about 26 mm, the outer diameter was about 30 mm, the thickness was about 2 mm, and the inner height was about 7.5 mm. Using these sensor housing dimensions, six new load sensors assemblies were prepared. The sensors were calibrated using the 3342 Instron. Input and output voltages, were recorded about every 30 seconds with the 34970A Agilent for the total about fourteen hours of testing. Loads of about 90N, 140N, and 180N were applied to the sensors for about two hours with about a two hour rest period in between each load, as shown in FIG. 7. The sensors were not rezeroed during this test in order to assess raw drift. The output voltages from the sensors were first normalized to the input voltage then converted to load values in Newtons using a calibration transfer function. Full scale drift percentage was calculated for both the return to zero and load conditions.

Figure 8:
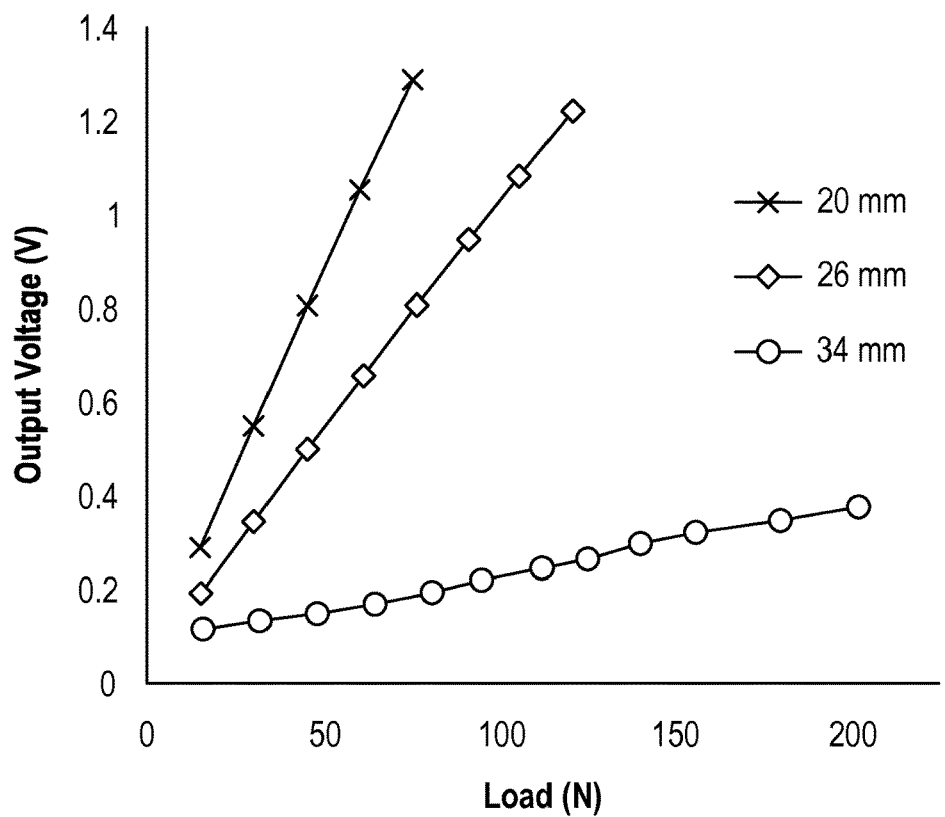
FIG. 8 illustrates the effects of varying the diameter of the housing of the working example on load sensor sensitivity with a sensor height of 9 mm.

The average two-hour drift at loads of about 90, 140 and 180N was about 0.52% (SD 0.04), 0.46% (SD 0.06), and 0.23% (SD 0.05), respectively of full scale output (about 500 N). The average drift for the approximately two-hour period prior to, in between, and after the loads were applied was about 0% (SD 0.00), 0.20% (SD 0.06), 0.23% (SD 0.07), and 0.25% (SD 0.07), respectively of full scale output (about 500 N), as shown in FIG. 8.

Cyclic Loading

The load sensor was designed to function and maintain accuracy for a minimum of 14,000 cycles, although other suitable load sensors and/or load profile monitoring devices may be configured for other numbers of cycles, or for continuous loading. Four of the load sensors used for drift testing were again used for cyclic testing. Cyclic testing was performed using a compression test instrument (Instron Model 1331) equipped with a 10 kN load cell and a NI SCB-68 DAQ interfaced with a custom LabView program to record from both the sensor and the Instron simultaneously. The Instron was programmed to cyclically load the sensors about 15,000 times from about 20-500 N at a frequency of 4 Hz. The sensors were not rezeroed during this test in order to assess the uncorrected effects of cyclic loading. Before the load sensors were cyclically loaded and after each set of about 5,000 cycles, a static load of about 400N was applied to the load sensor and the sensor output was recorded for about 5 seconds. The calibration transfer function used for the static drift testing was used to convert output voltage to load. The average load recorded by the sensor after each about 5,000 cycles was calculated by taking the mean of the entire approximately five seconds of recording.

Figure 9:
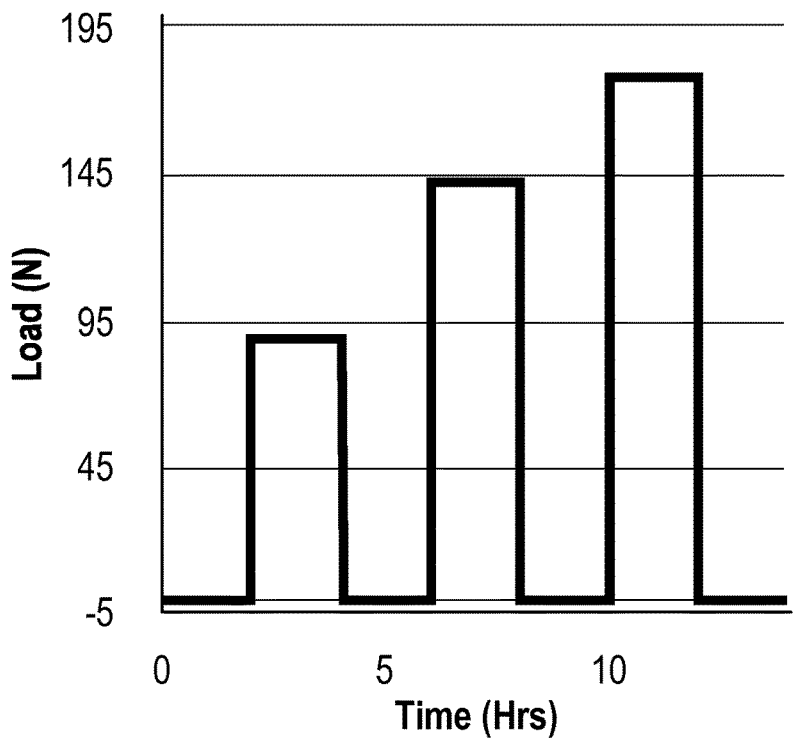
FIG. 9 illustrates the loads applied on the working example over time during a static drift test.
Figure 10:
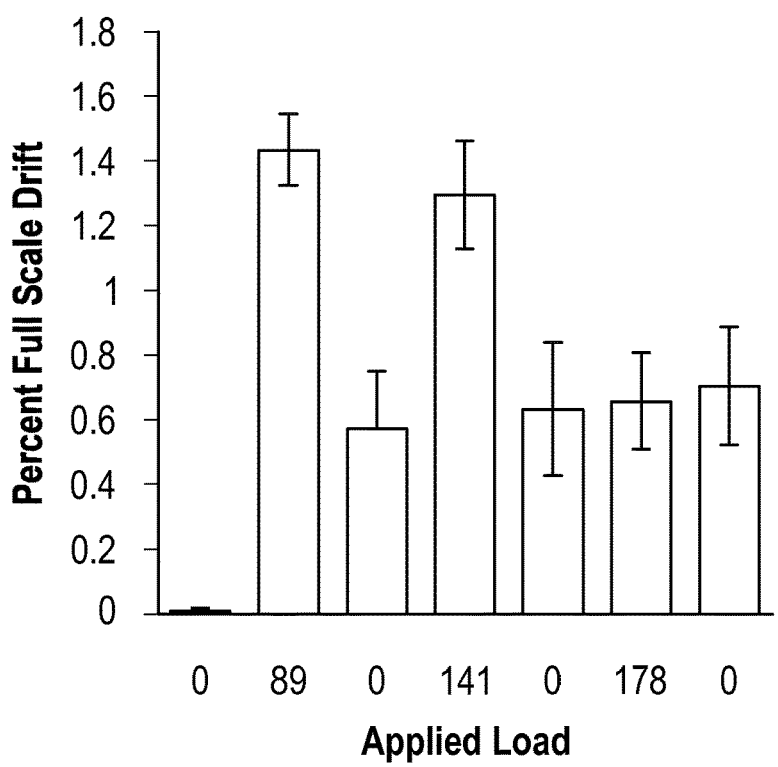
FIG. 10 illustrates the average drift for an approximately two hour period prior to, in between, and after loads were applied to various working example systems for measuring an under foot profile of a patient during a period of PWB.
Figure 11:
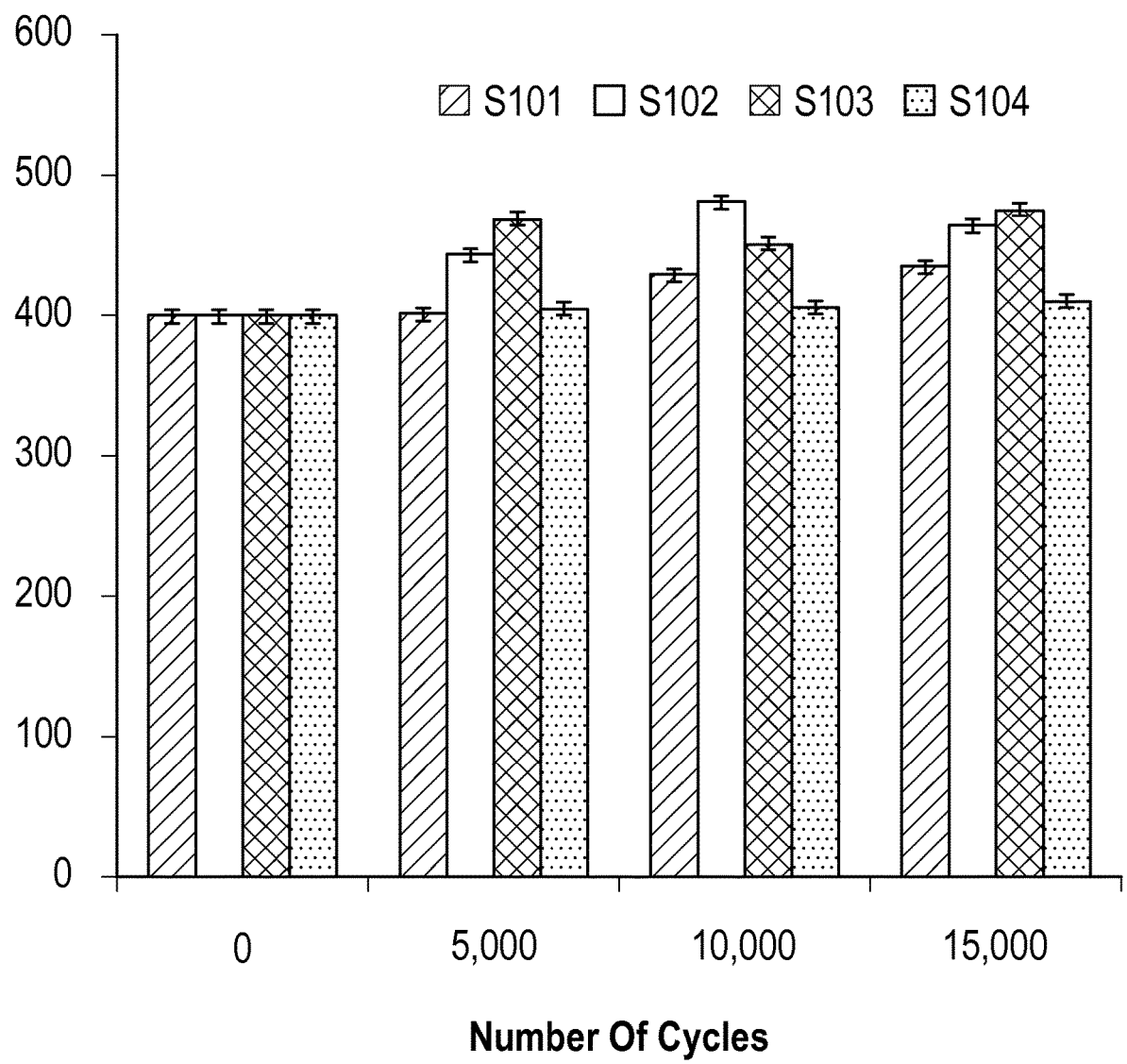
FIG. 11 illustrates the recorded sensor output after each set of 5,000 cycles for various working example systems for measuring an under foot profile of a patient during a period of PWB.

Cyclic testing showed varying amounts of drift between each recording period. The average drift for all the load sensors at the initial recording and after about 5,000, 10,000 and 15,000 cycles was about 0 (SD 0), 7 (SD 8), 10 (SD 8), and 11 (SD 7) percent, respectively. FIG. 9 displays the recorded sensor output after each set of 5,000 cycles for all the sensors. Sensor 104 had the lowest drift, reaching a maximum of about 2.0% after 15,000 cycles.

Treadmill Test in a Walking Boot Cast

To record the normal loads experience by the tibia during fracture recovery, the load sensor was designed to be placed in the heel region of a lower-leg immobilizer, which is generally worn during the entire rehabilitation period. Two subjects (one female about 50 kg, one male about 83 kg) walked on a treadmill for 30 steps at a speed of about 1.6 km/hr wearing the lower-leg immobilizer with the sensor placed under the heel. Two conditions were tested. The first was without the straps of the lower-leg immobilizer fastened. The second was with the straps securely fastened. A new load sensor was built and calibrated prior to testing. The load sensor's input and outputs were connected to NI USB-6210 DAQ (National Instruments, Austin, USA)

which powered the sensor with about 5V DC and recorded the ratiometric voltage output at about 100 Hz sampling frequency. The load sensor voltage output was recorded for the entire duration of testing. The raw load sensor voltage output was converted to load using a linear calibration transfer function. Using a peak detection function in Matlab, the maximum and minimum tibial loads were extracted from the load profile. A paired student T-test was used to compare the peak loads between strap and no strap condition, and a non-paired student T-test was used to compare the peak loads between the two subjects; P values of less than about 0.05 determined statistical differences.

The average peak load for the male subject for the no strap and the strap condition were about 240 N (SD 13) and about 215 N (SD 17) respectively. The average peak load for the female subject for the no strap and the strap condition were about 234 N (SD 15) and about 188 N (SD 14), respectively. The student T-test comparing the no strap and strap condition for both subjects led to the conclusion that there was a statistically significant difference between the strap and no-strap condition (P≤about 0.05). The student T-test between the male and female subject for both conditions also led to the conclusion of a statistically significant difference between the male and female subjects in this study (P≤about 0.05).

Providing Feedback to Users and Physicians

As mentioned above, lower extremity fractures are often hindered by complications during recovery. Proper management of a lower extremity fracture may rely on patients being able to place a certain percentage of their weight on the limb repeatedly. In some cases, patients are either unable to do so, or may do so in a manner that is not in compliance with the physician's recommended range of activity. These patients (and their physicians) may be unaware that they are acting outside the recommend range of activity.

Figure 12:
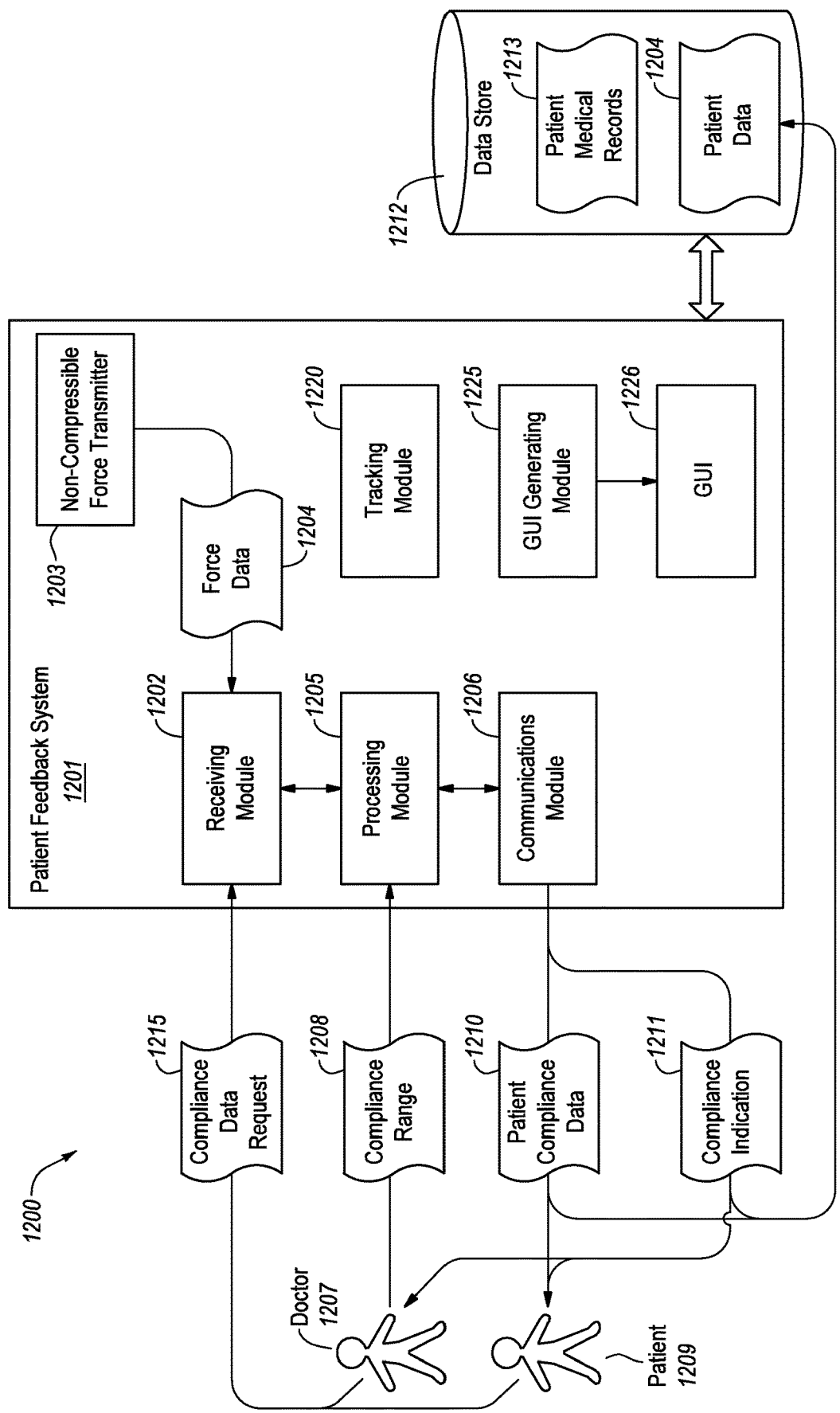
FIG. 12 illustrates a computer architecture in which embodiments described herein may operate including providing user feedback regarding compliance with a set of PWB criteria.

FIG. 12 describes a patient feedback system 1201 that includes various modules and other elements that provide feedback to users and physicians. The patient feedback system may be provided using one or more computer systems. These computer systems may include special purpose or general-purpose computers including computer hardware, such as, for example, one or more processors and system memory, as discussed in greater detail below. Embodiments described herein also include physical and other computer-readable media for carrying or storing computer-executable instructions and/or data structures. Such computer-readable media can be any available media that can be accessed by a general purpose or special purpose computer system. Computer-readable media that store computer-executable instructions in the form of data are computer storage media. Computer-readable media that carry computer-executable instructions are transmission media. Thus, by way of example, and not limitation, embodiments described herein can comprise at least two distinctly different kinds of computer-readable media: computer storage media and transmission media.

Computer storage media includes RAM, ROM, EEPROM, CD-ROM, solid state drives (SSDs) that are based on RAM, Flash memory, phase-change memory (PCM), or other types of memory, or other optical disk storage, magnetic disk storage or other magnetic storage devices, or any other medium which can be used to store desired program code means in the form of computer-executable instructions, data or data structures and which can be accessed by a general purpose or special purpose computer.

A "network" is defined as one or more data links and/or data switches that enable the transport of electronic data between computer systems and/or modules and/or other electronic devices. When information is transferred or provided over a network (either hardwired, wireless, or a combination of hardwired or wireless) to a computer, the computer properly views the connection as a transmission medium. Transmission media can include a network which can be used to carry data or desired program code means in the form of computer-executable instructions or in the form of data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC"), and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that various embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. Embodiments described herein may also be practiced in distributed system environments where local and remote computer systems that are linked (either by hardwired data links, wireless data links, or by a combination of hardwired and wireless data links) through a network, each perform tasks (e.g. cloud computing, cloud services and the like). In a distributed system environment, program modules may be located in both local and remote memory storage devices.

In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

For instance, cloud computing is currently employed in the marketplace so as to offer ubiquitous and convenient on-demand access to the shared pool of configurable computing resources. Furthermore, the shared pool of configurable computing resources can be rapidly provisioned via virtualization and released with low management effort or service provider interaction, and then scaled accordingly.

A cloud computing model can be composed of various characteristics such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud computing model may also be deployed using different deployment models such as private cloud, community cloud, public cloud, hybrid cloud, and so forth. In this description and in the claims, a "cloud computing environment" is an environment in which cloud computing is employed.

Additionally or alternatively, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), and other types of programmable hardware.

Still further, system architectures described herein can include a plurality of independent components that each contribute to the functionality of the system as a whole. This modularity allows for increased flexibility when approaching issues of platform scalability and, to this end, provides a variety of advantages. System complexity and growth can be managed more easily through the use of smaller-scale parts with limited functional scope. Platform fault tolerance is enhanced through the use of these loosely coupled modules. Individual components can be grown incrementally as business needs dictate. Modular development also translates to decreased time to market for new functionality. New functionality can be added or subtracted without impacting the core system.

Thus, the patient feedback system 1201 of computing environment 1200 may include or comprise any type of local or distributed computing system described above. The patient feedback system 1201 itself includes a receiving module 1202 that receives force data 1204 from a non-compressible force transmitter 1203. The non-compressible force transmitter may be any type of transmitter and may be configured to transmit detected forces including pressure. For example, the force transmitter 1203 may detect forces applied to a leg or foot when walking or otherwise moving. As explained above, the force transmitter may include a fluid or gel that may be selected to transmit pressure from one surface (e.g. on the heel of a foot brace) to a pressure sensor (1506 in FIG. 15). Optionally, the fluid or gel may be substantially incompressible. As a result, as a force is applied to the force transmitter 1203, the gel or fluid may experience minimal or no compression, and may instead develop a pressure therein, with the pressure being related to the applied load. Alternatively, the force transmitter 1203 may be some other incompressible or substantially incompressible material, including a solid material, biasing mechanism, or other material, or any combination of the foregoing.

In some embodiments, the non-compressible force transmitter 1203 may further include an accelerometer configured to monitor limb acceleration. This limb acceleration may be correlated to limb loading. The data may be stored with the limb loading data, and may be processed in a similar manner. The accelerometer may provide, for example, an indication of how many footsteps the user has taken over a certain period of time (hour, day, week, etc.). The accelerometer may also provide an indication of the speed of the user's footsteps. The user's speed and/or number of footsteps may provide additional factors that can be used to determine whether a user is acting within the physician's prescribed PWB compliance range.

The processing module 1205 may receive the force data 1204 detected by the pressure sensor and transmitted by the force transmitter 1203. The processing module determines whether the user or patient (used interchangeably herein) 1209 is within a predefined compliance range. The compliance range indicates a recommended range of limb loading during a PWB period (i.e. a range of weight that can be applied to the fractured limb). This compliance range 1208 may be prescribed by a physician (doctor 1207). The compliance range may indicate a number of steps, a range of force or load applied per step, a range of pressure per hour/day/week or other time period. The range may be customized for each patient. For instance, if patient 1209 has a particularly bad fracture, the compliance range 1208 would be smaller (i.e. it would include fewer steps, or a smaller amount of force per time period). Alternatively, if the patient 1209 has only a slight fracture, the compliance range may be higher. The range may also be tailored to the patient based on his or her height, weight, body type, range of movement, or other factors.

The processing module 1205 may access the prescribed compliance range and compare it to the patient's compliance data 1210 as received from the non-compressible force transmitter 1203. If the patient is outside the compliance range (either by taking too few steps, or too many steps, or by stepping with too much pressure), the doctor 1207 and/or the patient 1209 may be notified using communications module 1206.

The communications module 1206 may include any type of hardware and/or software used in wireless or wired data transmission. In some embodiments, a wired connection may be attached to the non-compressible force transmitter to transmit the patient's compliance data 1210. In other embodiments, a wireless transceiver may be placed within the non-compressible force transmitter 1203 to transmit the patient's compliance data 1210 and/or compliance indications 1211 to various entities including the doctor 1207, the patient 1209 and a data store 1212 that stores the patient's medical records 1213. The data store may be local or remote, physical or virtual, distributed or centrally located. In some cases, transfer of all the patient's force data (to any of the aforementioned entities) could result in excessive power consumption, reducing battery life of the patient feedback system 1201.

Thus, at least in some embodiments, for each stride, as well as for load maximum, values are calculated and selectively transmitted in groups of data to the patient, physician and or data store. Raw compliance data may be stored on a secure digital (SD) card and may be transferred to the physician database on-demand, when requested (e.g. during a patient's visit). Digitally determining load values involves algorithms that search and evaluate the stream of force data. To reduce power consumption, a power-efficient, analog envelope and peak detection circuit may be used, reducing the need for continuous search for characteristic data points. The wireless data transceiver may be an embedded transceiver embedded on an integrated microcontroller or radio system. Moreover, to conserve power, the force transmitter may have a sleep mode that can be regulated by activity of an accelerometer or by determining that the force sensors have not detected loads for a specified period of time.

Figure 16:
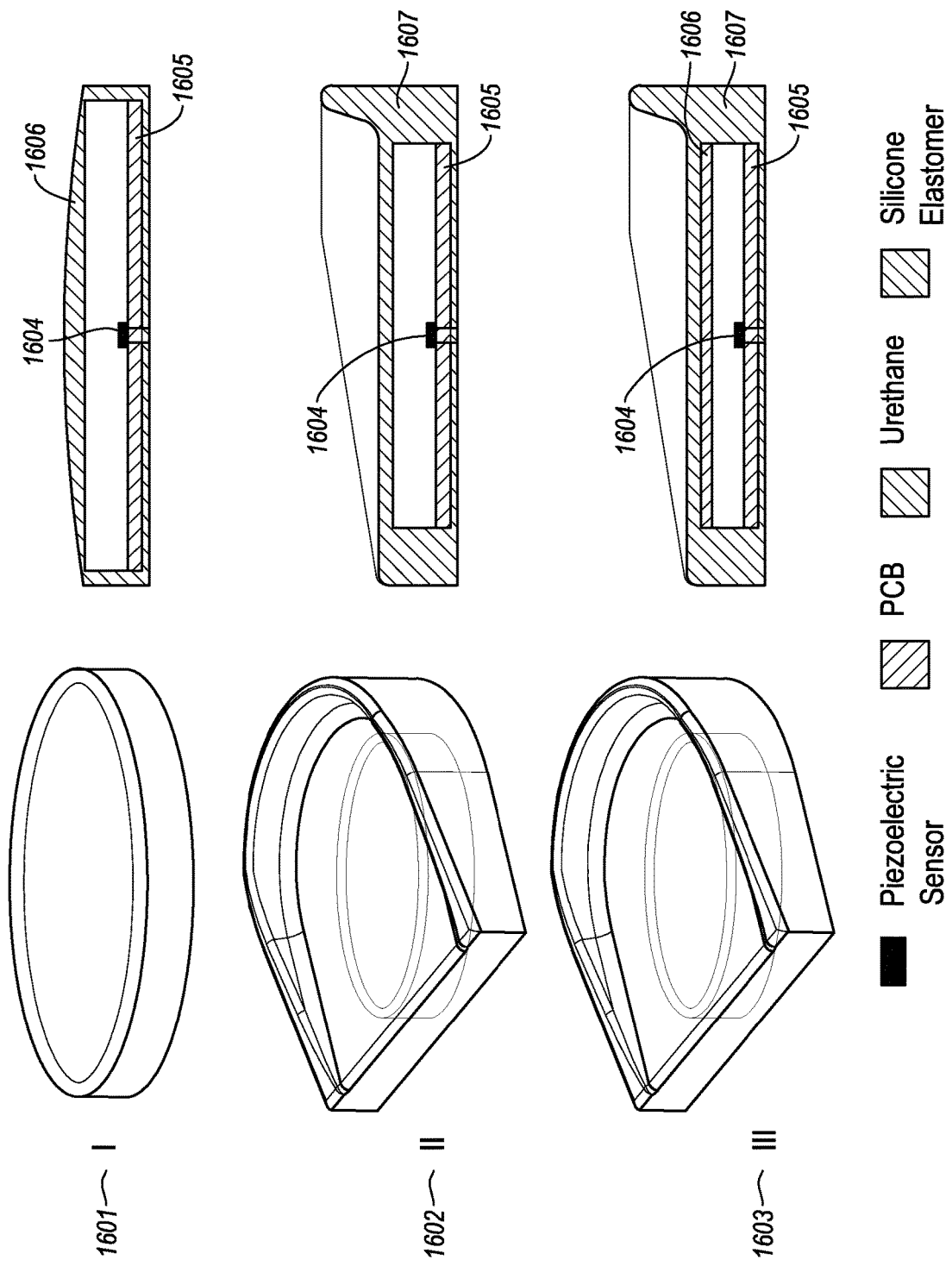
FIG. 16 illustrates various alternative embodiments of a non-compressible force transmitter.

In some embodiments, the non-compressible force transmitter 1203 of the patient feedback system 1201 is positioned in the heel of a foot, ankle or leg brace. The brace may include housing oriented with respect to the user's leg, heel or forefoot. The housing may include a cavity for various components including the non-compressible force transmitter 1203 and a pressure sensor that detects pressure within the housing. Three different embodiments are illustrated in FIG. 16. It will be understood that these are merely three of many different embodiments for the non-compressible force transmitter 1203. In embodiment I (1601), a piezoelectric sensor 1604 is placed on a printed circuit board (PCB) 1605. The printed circuit board may be surrounded by a urethane structure 1606. In embodiment II (1602), the piezoelectric sensor 1604 and PCB 1605 may be surrounded by a silicone elastomer 1607, while in embodiment III (1603), the piezoelectric sensor 1604, PCB 1605 and urethane structure 1606 may all be encased in a silicone elastomer shell 1607. Each of these embodiments provides varying levels of structural support and protection for the piezoelectric sensor and PCB.

The piezoelectric (pressure) sensor may be configured to monitor limb load of a user (i.e. patient 1209) during a period of partial weight bearing (PWB). The force data 1204 may be transmitted by the communications module 1206 to the user, the user's physician and/or to data store with the user's medical records. The user's data may be encrypted before it is sent, and the data may be sent over a secure connection established using any of a variety of different security protocols. In some cases, the user's data is compressed or otherwise processed to remove unwanted or unnecessary data. This, in turn, reduces the amount of data that is transmitted by the communications module 1206.

Figure 17:
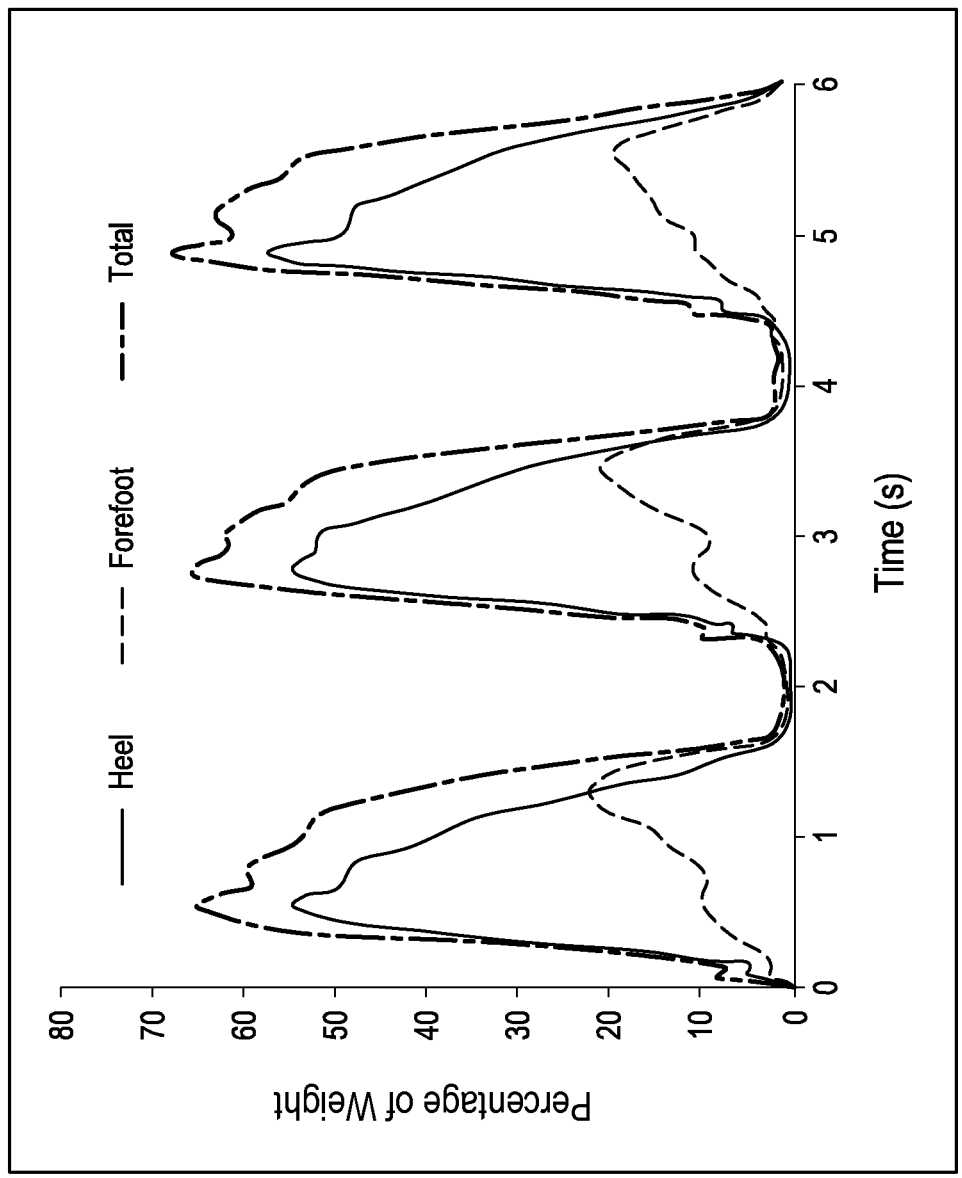
FIG. 17 illustrates a graphical timeline of force data on a user's heel and forefoot.

The raw or processed force data 1204 and/or compliance data 1210 may be displayed in a chart showing the user's movement over a specified period of time. The graphical user interface (GUI) generating module 1225 may generate a GUI 1226 that shows various types of data, including compliance and force data. The GUI may show raw data such as that shown in FIG. 17, where an amount of pressure is tracked over time for a patient's heel and forefoot. Additionally or alternatively, the GUI 1226 may show charts that illustrate the user's level of compliance with the predefined compliance range over a specified period of time.

Figure 18:
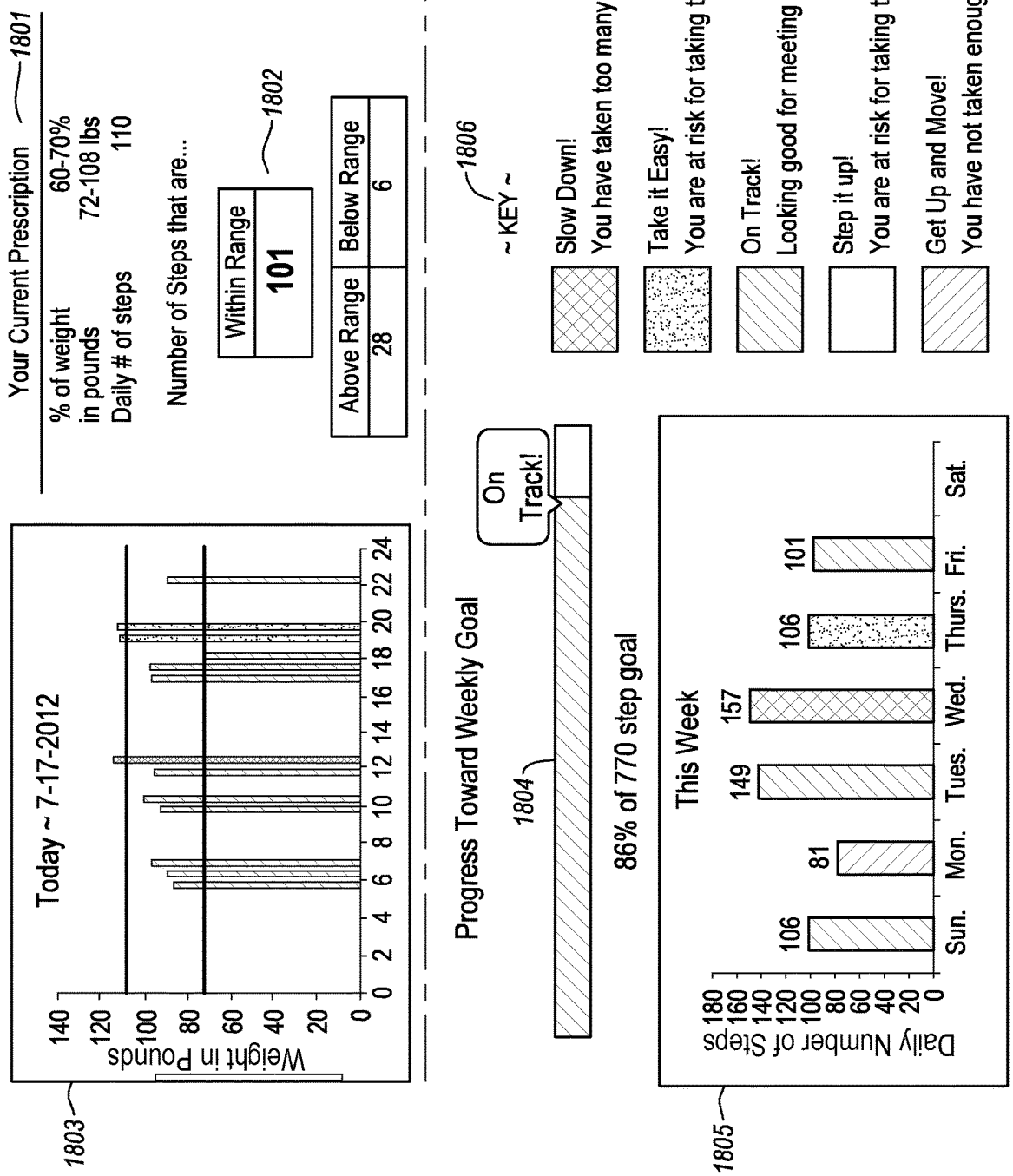
FIG. 18 illustrates an example graphical user interface (GUI) for providing user feedback regarding compliance with a set of PWB criteria.

For instance, element 1801 of FIG. 18 shows a user's current compliance prescription (i.e. the patient is to try for a daily number of 110 steps at 60-70% percent of their weight. Element 1802 shows that the patient had 101 steps that day that were in compliance, 28 steps that wee above the range, and six steps that were below the range. These steps may be graphically shown in graph 1803. Based on this information, other graphs may be generated such as a weekly chart 1805 that shows the user's compliance data for a week. The bars show how many steps the user took each day, and color-coding (as described in the key 1806) indicates what the user is to do (e.g. take fewer or more steps, or stay on track). A goal bar 1804 may show the user where they are on a compliance scale for the week, and may easily check to see whether they should take more or fewer steps.

This compliance data may be dynamically incorporated into a GUI on-demand, whenever the user (or physician) requests it. In some cases, the patient feedback system 1201 may track the number of times the patient views his or her movement or compliance data. The GUI 1226 may include multiple different graphical displays (e.g. for each time period (hour, day, week, etc., for a goal tracker, for a current prescription indication and others)), and may be configurable by the user or physician. The patient feedback system 1201 may also use tracking module 1220 to track the number of times each graphical display is viewed by the user or physician. In some cases, the GUI may show different information for the user and the physician. For instance, the GUI 1226 may show certain forms of feedback throughout the PWB period, and may show the physician a more cumulative view of the feedback data during a follow-up appointment.

The communications module 1206 may communicate a compliance indication 1211 as determined by the processing module 1205. The compliance indication may indicate whether the patient is complying with the prescribed compliance range 1208, and may also indicate the degree of compliance (e.g. a percent over or under or an amount of steps over or under the prescribed number, etc.). The compliance indication 1211 sent to the physician 1207 allows the physician to make informed decisions regarding the patient 1209. As mentioned above, the compliance range is customizable for each user. The compliance range may also be changed or updated as the patient progresses through his or her recovery. The user's compliance to any given compliance range may be determined at a specified periodic rate, and the corresponding compliance data may likewise be stored at that rate.

For example, the physician may indicate that compliance is to be determined hourly, daily, weekly, or at another specified time interval. Similarly, notifications of the user's compliance may be transmitted at a customizable, periodic rate, or on-demand. The specified periodic rate may be provided by the user's physician or other medical professional. The data representing the user's compliance with the predefined compliance range may be automatically synchronized to the user's medical records at specified intervals using a secure data channel. Moreover, the physician may be automatically alerted if the user is outside of the predefined compliance range by a specified threshold amount (either over or under the specified compliance range).

Figure 13:
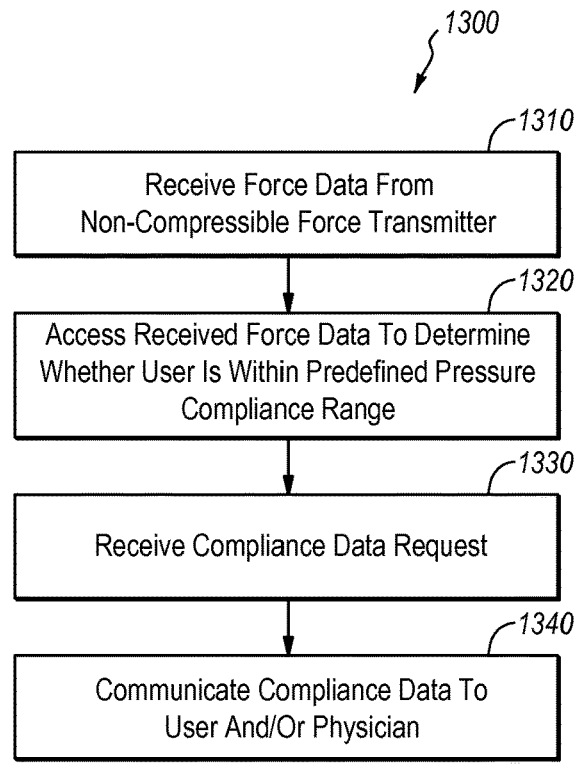
FIG. 13 illustrates a flowchart of an example method for providing user feedback regarding compliance with a set of PWB criteria.

Turning now to FIG. 13, a method 1300 is illustrated for providing user feedback regarding compliance with a set of partial weight bearing (PWB) criteria. The method 1300 will now be described with frequent reference to the components and data of environment 1200.

Method 1300 includes an act of receiving force data 1204 from a non-compressible force transmitter 1203 that is assigned to a user 1209 (act 1310). The processing module 1205 of the patient feedback system 1201 accesses the force data received from the non-compressible force transmitter to determine whether the user is within a predefined pressure compliance range 1208, where the pressure compliance range specifies a prescribed range of pressure that is to be applied during a PWB period (act 1320). The receiving module 1202 receives a compliance data request 1215 from the user 1209 and/or the user's physician 1207 (act 1330). Then, in response to the request, the communication module 1206 wirelessly (or otherwise) communicates compliance data 1210 representing the user's compliance with the prescribed range of pressure 1208 during the PWB period to the user and/or the user's physician (act 1340). This data may be stored in data store 1212 and/or used by GUI generating module 1225 to dynamically generate a GUI 1226 for the user or the physician. The user may then view the GUI and alter their behavior accordingly. Similarly, the physician may view the GUI and send an updated compliance prescription to the user indicating an updated compliance range based on the user's activity.

Figure 15:
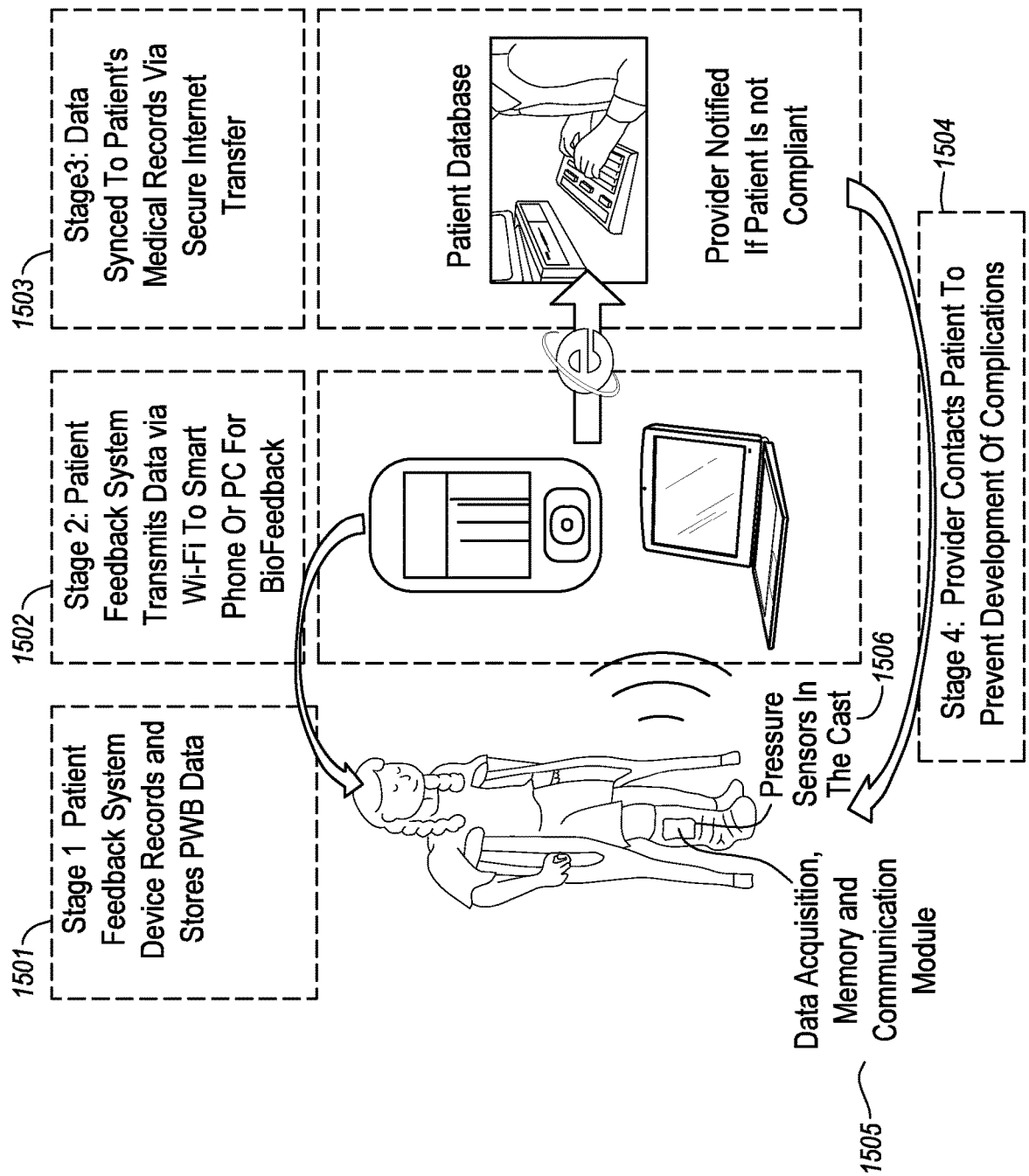
FIG. 15 illustrates an embodiment in which force data is gathered and stored to determine users' compliance with a predefined pressure compliance range.

FIG. 15 generally shows such a process. In stage 1 (1501), the patient feedback system (1201) may use sensors to determine a patient's movements and forces (or loads) applied to their legs. Using the patient feedback system, physicians or other users may collect data on patient limb loading and correlate it to fracture healing outcomes. The patient feedback system may use data driven protocols to provide feedback to the patient and to the clinician, as described in method 1300 above. Such an approach may not only enable clinicians to take a more proactive approach to fracture care and thereby reduce complications, improve outcomes and lower costs, but also return autonomy to patients and empower them to improve their treatment compliance and participation in their own health care.

As outlined above, fractured bones heal more quickly when they have an appropriate blood supply. Fractured bones also heal more quickly when some amount of loading or pressure is applied to the bones. This amount cannot be exceeded, however, without stunting the desired healing. Blood supply is needed to bring the cells, cytokines and other organic components necessary for bone formation. Mechanical loading and strain are necessary to activate osteogenic cells to encourage them to secrete new bone matrix. Excessive motion of the fractured fragments or an unstable mechanical environment at the initial stages of healing has been shown to inhibit bone healing.

In some embodiments, a micromachined pressure sensor 1506 may be packaged in a partially constrained silicone gel and used to continuously provide force measurements (see embodiments 1601-1603 of FIG. 16). The pressure sensor may, at least in some cases, be a piezoresistive pressure sensor. The piezoresistive pressure sensor may be converted into a load sensor by packaging the sensor in a silicone gel force-transduction media enclosed within a semi-rigid case. Since the area to which the load is applied is held constant, the force can be calculated from the pressure measurements. The pressure sensor in one embodiment may have desirable properties including high linearity (correlation coefficient of 1), low static drift (<1%) low dynamic drift (<3%), and low hysteresis, and other qualities that bode well for long-term monitoring. Sensor packaging can be adjusted to improve device performance. As described above, FIG. 16 displays several heel sensor designs. Patients may be monitored when ambulating in a walking boot fitted with the sensor.

Accordingly, at least in some cases, there may be a range of PWB activity that will facilitate fracture healing. Extreme variations from this range are thought to delay healing of the fracture. This range 1208 includes the amount of weight that is to be placed on the limb, as well as a range for the number of cycles in which the load is to be applied to the limb needed (e.g. on a daily/weekly basis, etc.) (e.g. prescription 1801 of FIG. 18). Healing time and the number of complications may be reduced by providing feedback to patients that guides them to keep their limb loading within a prescribed range. The feedback may be provided post-activity, or in real-time as the user is applying weight to the limb. Thus, the prescribed range of PWB activity may include a prescribed weight range and a prescribed number of steps.

The patient feedback system measures PWB behavior for certain period of time (e.g. two to six weeks) and reports the data to the patient and/or the clinician using the patient's personal computer and/or "smart phone" over a network connection (e.g. using a data acquisition, memory and communication module 1505 in Stage 2 (1502) of FIG. 15). The data reported to the patient will provide feedback to the patient regarding their compliance to the PWB prescription. The PWB monitoring data will be synched to the patient's medical records and will notify the clinician if the patient is dangerously out of compliance so the clinician can intervene before complications develop (Stage 3 (1503) of FIG. 15). The patient feedback system device design will enable incorporation into any walking boot cast and may include one or more of the following components: (1) a load monitoring component in the form of an insole insert, (2) an on-board microprocessor and data storage component to store and analyze raw data (i.e. find peak loading), and (3) a wireless data transfer system that will transfer data to a personal computer and/or smart phone.

Patients may be given software to install on their personal computer or smart phone. The software downloads the data from the patient feedback system to an online server. In some cases, the data may also be automatically synchronized to the patient's medical records 1213 using a secure encrypted data transfer protocol. If the patient is dangerously out of compliance with the prescribed PWB range, a message may be sent to the patient's clinician. The clinician can either call the patient to discuss the overuse of the limb, or have a scheduling team call the patient to schedule a clinic visit to evaluate the patient for any signs of complications and to encourage the patient to comply with the prescribed use range (Stage 4 (1504) of FIG. 15. Software installed on the client's computing systems and/or on the clinician's computing systems may be configured to display the patient's limb loading in a variety of graphical formats in GUI 1226. For instance, the formats may include waveforms, trend plots, figural or object displays and other displays that are able to illustrate relationships between physiological variables.

The types of data to report to the patient may include information regarding the magnitude and number of steps taken (see 1803 and 1805 of FIG. 18). This data can be separated into different subsets including: number of steps that are within the prescribed range, number of steps over the prescribed range, number of steps below the prescribed range, and progress toward weekly or monthly goals for the number of steps recommended (see 1802, 1804 and 1805 of FIG. 18). Color-coding can be used to warn the patients if they have taken a dangerous number of steps outside the prescribed range (according to key 1806). Too many steps above the prescribed range can put the user at risk for complications. Too few steps below the prescribed range and not enough within the prescribed range may put the patient at risk for a delayed union. Several graphs may be displayed on the same screen. One graph could be a weekly histogram of the step count (1803), while another could be a graph that shows status towards weekly step goals (1804). As will be understood by one skilled in the art, substantially any number of graphs may be shown in any order, and in any fashion.

Figure 14:
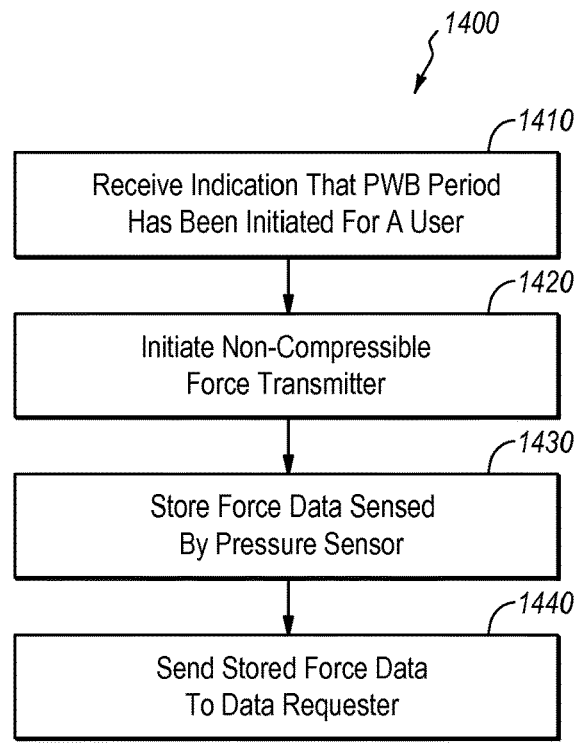
FIG. 14 illustrates a flowchart of an example method for gathering and storing force data to determine users' compliance with a predefined pressure compliance range.

Turning now to FIG. 14, a method 1400 is provided for gathering and storing force data to determine users' compliance with a predefined pressure compliance range. The method 1400 will now be described with frequent reference to the components and data of environment 1200.

Method 1400 includes an act of receiving an indication that a period of partial weight bearing (PWB) has been initiated for user 1209 (act 1410). In response, the patient feedback system 1201 initiates a non-compressible force transmitter 1203 that is assigned to the user. The non-compressible force transmitter may be positioned both within a cavity of a housing oriented with respect to the user's leg and adjacent to a pressure sensor to transmit pressure within the housing (act 1420). The patient feedback system 1201 may then store, at specified intervals, one or more portions of force data 1204 sensed by the pressure sensor, where the force data indicates the user's compliance with a prescribed range of pressure 1208 that is to be applied during the PWB period (act 1430). Then, upon receiving a request for stored force data, the stored force data is sent to the data requester (act 1440). Thus, in this manner, the patient feedback system 1201 may monitor a patient's compliance with a prescribed pressure or movement range. That patient's compliance data may be stored and later sent to the patient and/or the patient's physician on-demand. The data may be presented in a GUI that clearly shows how well the user is complying with the prescribed compliance range. If the user is too far off the compliance range, the physician may notify the patient and may send an updated compliance range where applicable.

Accordingly, a patient feedback system is provided that monitors a patient's use of a healing limb. The patient's compliance data is transmitted to the patient's personal computer or smart phone so the patient can track his or her compliance with a prescribed range of use. The patient's compliance data is also transmitted to a physician so the physician can monitor the patient's compliance with the prescribed ranged of use. Still further, the patient's compliance data may be automatically synchronized to his or her medical records using a wireless data transmitter.

The scope of the invention is not limited to the aforementioned example embodiments. Moreover, a person of ordinary skill in the art will understand that aspects of one or more of the foregoing example embodiments may be combined with aspects of one or more other of the foregoing examples to define yet further embodiments within the scope of the invention. It should also be noted that nothing herein constitutes, or should be construed as constituting, a 'critical' or 'essential' element of any particular embodiment, or group of embodiments.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for providing user feedback regarding compliance with a set of partial weight bearing (PWB) criteria including a load compliance range, the system including:
   a single load profile monitoring device that receives force data from a pressure sensor positioned adjacent to a substantially non-compressible pressure transmitter, wherein the single load profile monitoring device is sized and configured to measure a load profile in both a ball region of a foot and a heel region of the foot;
   the substantially non-compressible pressure transmitter being configured to transfer force to the pressure sensor, wherein:
      the substantially non-compressible pressure transmitter is positioned within a cavity of a housing,
      the pressure sensor is configured to float or otherwise move within the substantially non-compressible pressure transmitter to change location and/or orientation,
      the pressure sensor positioned:
         at a non-parallel angle with respect to a bottom surface of the housing, and
         offset from a line-of-action of a force applied to the housing; and
      the housing comprises an aperture that provides a reference atmospheric pressure to the pressure sensor;
   a processing module that accesses the force data received from the pressure sensor to determine whether the user is within a predefined load compliance range, the load compliance range specifying a prescribed range of load that is to be applied during a PWB period; and
   a communications module that, upon receiving a compliance data request, communicates compliance data representing the user's compliance with the prescribed range of load during the PWB period to at least one of the user and the user's physician, wherein the user's compliance is determined at a rate that is specified by a medical professional.

2. The system of claim 1, wherein:
   the housing is configured to be oriented with respect to the user, said housing including a flexible upper surface, said flexible upper surface defining at least a portion of the cavity of the housing;
   the pressure sensor configured to monitor a load profile of the user during the PWB period, the pressure sensor being located at least partially within the cavity; and
   the substantially non-compressible pressure transmitter positioned within the cavity and adjacent to the pressure sensor to transmit pressure within the housing to the pressure sensor.

3. The system of claim 1, wherein the aperture provides a pathway for a communication between the pressure sensor and a storage device.

4. The system of claim 3, wherein the substantially non-compressible pressure transmitter further includes an accelerometer that monitors limb acceleration.

5. The system of claim 1, wherein a wireless communications module communicates at least one of raw and processed compliance data to at least the user in response to the compliance data request.

6. The system of claim 5, wherein the compliance data is displayed in a graphical user interface (GUI) that includes a chart showing the user's compliance over a specified period of time.

7. The system of claim 6, wherein the chart displayed in the GUI shows the user's level of compliance with the predefined compliance range over a specified period of time.

8. The system of claim 1, further comprising a tracking module that tracks the number of times the user views his or her compliance data.

9. The system of claim 8, wherein the tracking module tracks the number of times each graphical display is viewed by the user.

10. The system of claim 1, wherein the compliance data sent to the user's physician using the communications module allows the user's physician to make informed decisions regarding the user.

11. The system of claim 1, wherein the processing module customizes the predefined load compliance range for each user.

12. The system of claim 1, wherein the force data is stored within a local, physically removable storage medium.

13. The system of claim 1, wherein the compliance data is processed at least in part by an analog envelope and peak detection circuit.

14. The system of claim 1, wherein the processing module automatically synchronizes the compliance data representing the user's compliance with the predefined compliance range to the user's medical records.

15. The system of claim 1, wherein the communications module automatically alerts the user's physician if the user is outside of the predefined compliance range by a specified threshold amount.

16. A computer-implemented method for providing user feedback regarding compliance with a set of partial weight bearing (PWB) criteria, the method comprising:
   receiving force data from a pressure sensor positioned in physical communication with a substantially non-compressible pressure transmitter that is assigned to a user, wherein:
      the substantially non-compressible pressure transmitter is positioned within a cavity of a housing,
      the pressure sensor comprises a piezoresistive pressure sensor that has been converted into a load sensor by packaging the piezoresistive pressure sensor in a silicone gel force-transduction media enclosed within a semi-rigid case,
      the pressure sensor is sized and configured to measure a load profile in both a ball region of a foot and a heel region of the foot,
      the pressure sensor is configured to float or otherwise move within the substantially non-compressible pressure transmitter to change location and/or orientation,
      the pressure sensor is positioned:
         at a non-parallel angle with respect to a bottom surface of the housing, and
         offset from a line-of-action of a force applied to the housing, and
      the housing comprises an aperture that provides a reference atmospheric pressure to the pressure sensor;
   accessing the force data received from the pressure sensor to determine whether the user is within a predefined load compliance range, the load compliance range specifying a prescribed range of load that is to be applied during a PWB period;
   receiving a compliance data request from the user or the user's physician; and
   communicating compliance data representing the user's compliance with the prescribed range of load during the PWB period to the user or the user's physician, wherein the user's compliance is determined at a rate that is specified by a medical professional.

17. The computer-implemented method of claim 16, further comprising an act of dynamically generating a graphical user interface (GUI) that displays at least a portion of the accessed compliance data.

18. The computer-implemented method of claim 16, further comprising an act of receiving from the user's physician a compliance prescription indicating an updated compliance range based on the user's activity.

19. A computer system for gathering and storing force data to determine a user's compliance with a predefined pressure compliance range comprising:
   one or more processors;
   system memory;
   one or more computer-readable storage media having stored thereon computer-executable instructions that, when executed by the one or more processors, causes the computing system to perform at least the following:
      receive an indication that a period of partial weight bearing (PWB) has been initiated for a user;
      initiate a pressure sensor that is in physical communication with a substantially non-compressible pressure transmitter that is assigned to the user, wherein:
         the substantially non-compressible pressure transmitter is positioned both within a cavity of a housing oriented with respect to the user's leg and adjacent to the pressure sensor to transmit pressure within the housing,
         the pressure sensor is configured to float or otherwise move within the substantially non-compressible pressure transmitter to change location and/or orientation,
         the pressure sensor is positioned:
            at a non-parallel angle with respect to a bottom surface of the housing, and
            offset from a line-of-action of a force applied to the housing, and
         the housing comprises an aperture that provides a reference atmospheric pressure to the pressure sensor;
      store, at specified intervals, one or more portions of force data sensed by the pressure sensor, the force data indicating the user's compliance with a predefined pressure compliance range that is to be applied during the PWB period, wherein the specified intervals are specified by a medical professional; and
      upon receiving a request for stored force data, send the stored force data to the data requester.

* * * * *